(12) United States Patent
Firnberg et al.

(10) Patent No.: US 9,458,453 B2
(45) Date of Patent: *Oct. 4, 2016

(54) METHODS FOR EFFICIENT, EXPANSIVE, USER-DEFINED DNA MUTAGENESIS

(71) Applicant: THE JOHNS HOPKINS UNIVERSITY, Baltimore, MD (US)

(72) Inventors: Elad Firnberg, Baltimore, MD (US); Marc Alan Ostermeier, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/407,683

(22) PCT Filed: Jun. 12, 2013

(86) PCT No.: PCT/US2013/045487
§ 371 (c)(1),
(2) Date: Dec. 12, 2014

(87) PCT Pub. No.: WO2013/188578
PCT Pub. Date: Dec. 19, 2013

(65) Prior Publication Data
US 2015/0184150 A1    Jul. 2, 2015

Related U.S. Application Data

(60) Provisional application No. 61/658,607, filed on Jun. 12, 2012.

(51) Int. Cl.
C12P 19/34    (2006.01)
C12N 15/10    (2006.01)
C07H 21/04    (2006.01)

(52) U.S. Cl.
CPC ........... *C12N 15/1031* (2013.01); *C07H 21/04* (2013.01); *C12N 15/102* (2013.01); *C12P 19/34* (2013.01)

(58) Field of Classification Search
USPC ............................................. 435/6.12, 91.2
See application file for complete search history.

(56) References Cited

U.S. PATENT DOCUMENTS

2006/0051748 A1    3/2006    Hogrefe
2007/0191272 A1    8/2007    Stemmer et al.
2013/0045507 A1    2/2013    Huovinen et al.

FOREIGN PATENT DOCUMENTS

| EP | 1178109 A1 | 2/2002 |
|---|---|---|
| WO | 2005054492 A1 | 6/2005 |
| WO | 2011077004 A1 | 6/2011 |

OTHER PUBLICATIONS

International Search Report dated Sep. 13, 2013; International Application No. PCT/US2013/045487.
Ambler and Coulson (1991) A Standard Numbering Scheme for the Class A Beta-Lactamases. Biochemical Journal Letters 276: 269-272.

(Continued)

*Primary Examiner* — Kenneth Horlick
(74) *Attorney, Agent, or Firm* — Ward and Smith, P.A.; Jeffrey W. Childers

(57) ABSTRACT

The presently disclosed subject matter relates to modified Kunkel mutagenesis methods that use a thermostable DNA polymerase and a thermostable DNA ligase.

47 Claims, 7 Drawing Sheets

(56) References Cited

OTHER PUBLICATIONS

André et al. (1997) Fidelity and mutational spectrum of pfu DNA polymerase on a human mitochondrial DNA sequence. Genome Res 7: 843-852.
Araya and Fowler (2011) Deep mutational scanning: assessing protein function on a massive scale. Trends Biotechnol 29: 435-442.
Baldwin et al. (2008). Expanded molecular diversity generation during directed evolution by trinucleotide exchange 5 (trinex). Nucleic Acids Res, 36(13), e77.
Bi and Stambrook (1998). Site-Directed mutagenesis by combined chain reaction. Anal Biochem, 256(1), 137-40.
Blankenberg et al. "Galaxy: a web-based genome analysis tool for experimentalists". Current Protocols in Molecular Biology. Jan. 2010; Chapter 19:Unit 19.10.1-21.
Chung et al. (1989). One-Step preparation of competent *Escherichia coli*: Transformation and storage of bacterial cells in the same solution. Proc Natl Acad Sci U S A, 86(7), 2172-5.
Cunningham and Wells (1989) High-resolution epitope mapping of hGHreceptor interactions by alanine-scanning mutagenesis. Science 244: 1081-1085.
Denbigh (1944) Velocity and yield in continuous reaction systems. Trans. Faraday Soc 40: 352-373.
Dominy and Andrews (2003) Site-Directed mutagenesis by inverse PCR. Methods Mol Biol 235:209-23.
Drawz and Bonomo (2010) Three decades of β-lactamase inhibitors. Clin Microbiol Rev 23: 160.
Giardine et al., "Galaxy: a platform for interactive large-scale genome analysis." Genome Research. Oct. 2005; 15(10):1451-5.
Goecks et al. Galaxy: a comprehensive approach for supporting accessible, reproducible, and transparent computational research in the life sciences. Genome Biol. Aug. 25, 2010:11(8):R86.
Hames et al. (2005). Multiple-Mutation reaction: A method for simultaneous introduction of multiple mutations into the glpk gene of *Mycoplasma pneumoniae*. Appl. Environ Microbiol, 71(7), 4097-100.
Hogrefe et al. (2001). DNA polymerases from hyperthermophiles. Methods Enzymol, 334, 91-116.
Holland et al. (2011). Second generation sequencing allows for mtdna mixture deconvolution and high resolution detection of heteroplasmy. Croat Med J, 52(3), 299-313.
Kunkel (1985). Rapid and efficient site-specific mutagenesis without phenotypic selection. Proc Natl Acad Sci U S A, 82(2), 488-92.
Kunkel et al. (1991), Efficient site-directed mutagenesis using uracil-containing DNA. Methods Enzymol, 204, 125-39.
Kunkel et al. (1987), Rapid and efficient sitespecific mutagenesis without phenotypic selection. Methods Enzymol, 154, 367-82.
Lindahl and Nyberg (1972) Rate of depurination of native deoxyribonucleic acid. Biochemistry 11: 3610-3618.
Lindahl and Nyberg (1974) Heat-Induced deamination of cytosine residues in deoxyribonucleic acid. Biochemistry 13: 3405-3410.
Liu and Cropp (2012). A method for multi-codon scanning mutagenesis of proteins based on asymmetric transposons. Protein Eng Des Sel, 25(2), 67-72.
Meyerhans et al. (1990). DNA recombination during PCR. Nucleic Acids Res, 18(7), 1687-91.
Murakami et al. (2002). Random insertion and deletion of arbitrary number of bases for codon-based random mutation of dnas. Nat Biotechnol, 20(1), 76-81.
Nørholm (2010). A mutant pfu DNA polymerase designed for advanced uracil-excision DNA engineering. BMC Biotechnol, 10, 21.
PfuTurbo Cx hotstart DNA polymerase Instruction Manual, (2009) Catalog #600410, Revision A.01. Agilent Technologies.
Robin et al. (2011) In vitro efficiency of the piperacilin/tazobactam combination against inhibitor-resistant TEM and complex mutant TEM-producing clinical strains of *Escherichia coli*. J Antimicrob Chemother 66: 1052-1056.
Rogers and Weiss (1980). Exonuclease III of *Escherichia coli* K-12, an AP endonuclease. Methods Enzymol, 65(1), 201-11.
Sambrook et al. (2001). Molecular cloning: A laboratory manual (3 ed.). Cold Spring Harbor Laboratory Press.
Sohka et al. (2009). An externally tunable bacterial band-pass filter. Proc Natl Acad Sci U S A, 106(25), 10135-40.
Taylor and Weiss (1982). Role of exonuclease III in the base excision repair of uracil-containing DNA. J Bacteriol, 151(1), 351-7.
Trower (1994). Site-directed mutagenesis using a uracil-containing phagemid template. Methods Mol Biol, 31, 67-77.
Vakulenko et al. (1998) Selection and characterization of beta-lactam-beta-lactamase inactivator-resistant mutants following PCR mutagenesis of the TEM-1 beta-lactamase gene. Antimicrob Agents Chemother 42: 1542-1548.
Wassman et al. (2004). Predicting oligonucleotide-directed mutagenesis failures in protein engineering. Nucleic Acids Res, 32(21), 6407-13.
Weiss et al. (2000). Rapid mapping of protein functional epitopes by combinatorial alanine scanning. Proc Natl Acad Sci U S A, 97(16), 8950-4.
Restriction Requirement dated Jun. 26, 2015 from related U.S. Appl. No. 13/916,475.
Non-Final Office action dated Sep. 10, 2015 from related U.S. Appl. No. 13/916,475.

SEQUENCE LISTING

```
<160> NUMBER OF SEQ ID NOS: 25

<210> SEQ ID NO 1
<211> LENGTH: 25
<212> TYPE: DNA
<213> ORGANISM: Artificial Sequence
<220> FEATURE:
<223> OTHER INFORMATION: Oligonucleotide P320

<400> SEQUENCE: 1
gcagaaattc gaaagcaaat tcgac                                          25

<210> SEQ ID NO 2
<211> LENGTH: 26
<212> TYPE: DNA
<213> ORGANISM: Artificial Sequence
<220> FEATURE:
<223> OTHER INFORMATION: Oligonucleotide encoding a c542a mutation in
      the bla gene

<400> SEQUENCE: 2
gacaccacga tgcatgcagc aatggc                                         26

<210> SEQ ID NO 3
<211> LENGTH: 27
<212> TYPE: DNA
<213> ORGANISM: Artificial Sequence
<220> FEATURE:
<223> OTHER INFORMATION: Oligonucleotide to introduce random bases at
      codon position 42 in the bla gene
<220> FEATURE:
<221> NAME/KEY: misc_feature
<223> OTHER INFORMATION: n is A, C, G, or T
<220> FEATURE:
<221> NAME/KEY: misc_feature
<222> LOCATION: (13)..(15)
<223> OTHER INFORMATION: n is a, c, g, or t

<400> SEQUENCE: 3
gatcagttgg gtnnncgagt gggttac                                        27
```

```
<210> SEQ ID NO 4
<211> LENGTH: 30
<212> TYPE: DNA
<213> ORGANISM: Artificial Sequence
<220> FEATURE:
<223> OTHER INFORMATION: Oligonucleotide to introduce random bases at
      codon position 104 in the bla gene
<220> FEATURE:
<221> NAME/KEY: misc_feature
<223> OTHER INFORMATION: n is A, C, G, or T
<220> FEATURE:
<221> NAME/KEY: misc_feature
<222> LOCATION: (14)..(16)
<223> OTHER INFORMATION: n is a, c, g, or t

<400> SEQUENCE: 4
gaatgacttg gttnnntact caccagtcac                                     30

<210> SEQ ID NO 5
<211> LENGTH: 27
<212> TYPE: DNA
<213> ORGANISM: Artificial Sequence
<220> FEATURE:
<223> OTHER INFORMATION: Oligonucleotide to introduce random bases at
      codon position 182 in the bla gene
<220> FEATURE:
<221> NAME/KEY: misc_feature
<223> OTHER INFORMATION: n is A, C, G, or T
<220> FEATURE:
<221> NAME/KEY: misc_feature
<222> LOCATION: (13)..(15)
<223> OTHER INFORMATION: n is a, c, g, or t

<400> SEQUENCE: 5
cgtgacacca cgnnncctgc agcaatg                                        27

<210> SEQ ID NO 6
<211> LENGTH: 27
<212> TYPE: DNA
<213> ORGANISM: Artificial Sequence
<220> FEATURE:
<223> OTHER INFORMATION: Oligonucleotide to introduce random bases at
      codon position 238 in the bla gene
<220> FEATURE:
<221> NAME/KEY: misc_feature
<223> OTHER INFORMATION: n is A, C, G, or T
<220> FEATURE:
<221> NAME/KEY: misc_feature
<222> LOCATION: (13)..(15)
<223> OTHER INFORMATION: n is a, c, g, or t

<400> SEQUENCE: 6
aaatctggag ccnnngagcg tgggtct                                        27

<210> SEQ ID NO 7
<211> LENGTH: 27
<212> TYPE: DNA
<213> ORGANISM: Artificial Sequence
<220> FEATURE:
<223> OTHER INFORMATION: Oligonucleotide to introduce the A42G mutation
      in the bla gene

<400> SEQUENCE: 7
gatcagttgg gtggacgagt gggttac                                        27

<210> SEQ ID NO 8
<211> LENGTH: 36
<212> TYPE: DNA
<213> ORGANISM: Artificial Sequence
<220> FEATURE:
<223> OTHER INFORMATION: Oligonucleotide to introduce the E104K mutation
``` in the bla gene

<400> SEQUENCE: 8
ctcagaatga cttggttaag tactcaccag tcacag                36

<210> SEQ ID NO 9
<211> LENGTH: 34
<212> TYPE: DNA
<213> ORGANISM: Artificial Sequence
<220> FEATURE:
<223> OTHER INFORMATION: Oligonucleotide to introduce the M182T mutation
      in the bla gene

<400> SEQUENCE: 9
gtgacaccac gacgcctgca gcaatggcaa caac                  34

<210> SEQ ID NO 10
<211> LENGTH: 35
<212> TYPE: DNA
<213> ORGANISM: Artificial Sequence
<220> FEATURE:
<223> OTHER INFORMATION: Oligonucleotide to introduce the G238S mutation
      in the bla gene

<400> SEQUENCE: 10
gctgataaat ctggagccag tgagcgtggg tctcg                 35

<210> SEQ ID NO 11
<211> LENGTH: 36
<212> TYPE: DNA
<213> ORGANISM: Artificial Sequence
<220> FEATURE:
<223> OTHER INFORMATION: Oligonucleotide to introduce the M69L mutation
      in the TEM-1 gene

<400> SEQUENCE: 11
cccgaagaac gttttccaat gctgagcact tttaaa                36

<210> SEQ ID NO 12
<211> LENGTH: 30
<212> TYPE: DNA
<213> ORGANISM: Artificial Sequence
<220> FEATURE:
<223> OTHER INFORMATION: Oligonucleotide to introduce the Y105S mutation
      in the TEM-1 gene

<400> SEQUENCE: 12
tgacttggtt gagtcctcac cagtcacaga                       30

<210> SEQ ID NO 13
<211> LENGTH: 30
<212> TYPE: DNA
<213> ORGANISM: Artificial Sequence
<220> FEATURE:
<223> OTHER INFORMATION: Oligonucleotide to introduce the Y105D mutation
      in the TEM-1 gene

<400> SEQUENCE: 13
tgacttggtt gaggactcac cagtcacaga                       30

<210> SEQ ID NO 14
<211> LENGTH: 30
<212> TYPE: DNA
<213> ORGANISM: Artificial Sequence
<220> FEATURE:
<223> OTHER INFORMATION: Oligonucleotide to introduce the Y105N mutation
      in the TEM-1 gene -continued

<400> SEQUENCE: 14
tgacttggtt gagaactcac cagtcacaga                               30

<210> SEQ ID NO 15
<211> LENGTH: 28
<212> TYPE: DNA
<213> ORGANISM: Artificial Sequence
<220> FEATURE:
<223> OTHER INFORMATION: Oligonucleotide to introduce the S235T mutation
      in the TEM-1 gene

<400> SEQUENCE: 15
attgctgata aaactggagc cggtgagc                                 28

<210> SEQ ID NO 16
<211> LENGTH: 27
<212> TYPE: DNA
<213> ORGANISM: Artificial Sequence
<220> FEATURE:
<223> OTHER INFORMATION: Oligonucleotide to introduce the R244S mutation
      in the TEM-1 gene

<400> SEQUENCE: 16
gagcgtgggt ctagcggtat cattgca                                  27

<210> SEQ ID NO 17
<211> LENGTH: 31
<212> TYPE: DNA
<213> ORGANISM: Artificial Sequence
<220> FEATURE:
<223> OTHER INFORMATION: Oligonucleotide to introduce the N276D mutation
      in the TEM-1 gene

<400> SEQUENCE: 17
atggatgaac gagatagaca gatcgctgag a                             31

<210> SEQ ID NO 18
<211> LENGTH: 27
<212> TYPE: DNA
<213> ORGANISM: Artificial Sequence
<220> FEATURE:
<223> OTHER INFORMATION: Oligonucleotide to introduce the A42G mutation
      in the TEM-1 gene

<400> SEQUENCE: 18
gatcagttgg gtgggcgagt gggttac                                  27

<210> SEQ ID NO 19
<211> LENGTH: 36
<212> TYPE: DNA
<213> ORGANISM: Artificial Sequence
<220> FEATURE:
<223> OTHER INFORMATION: Oligonucleotide to introduce the E104K mutation
      in the TEM-1 gene

<400> SEQUENCE: 19
ctcagaatga cttggttaag tactcaccag tcacag                        36

<210> SEQ ID NO 20
<211> LENGTH: 27
<212> TYPE: DNA
<213> ORGANISM: Artificial Sequence
<220> FEATURE:
<223> OTHER INFORMATION: Oligonucleotide to introduce the M182Q mutation
      in the TEM-1 gene

<400> SEQUENCE: 20
cgtgacacca cgcagcctgc agcaatg                                      27

<210> SEQ ID NO 21
<211> LENGTH: 27
<212> TYPE: DNA
<213> ORGANISM: Artificial Sequence
<220> FEATURE:
<223> OTHER INFORMATION: Oligonucleotide to introduce the G238A mutation
      in the TEM-1 gene

<400> SEQUENCE: 21
aaatctggag ccgcagagcg tgggtct                                      27

<210> SEQ ID NO 22
<211> LENGTH: 27
<212> TYPE: DNA
<213> ORGANISM: Artificial Sequence
<220> FEATURE:
<223> OTHER INFORMATION: Oligonucleotide for position 42 in the TEM-1
      gene
<220> FEATURE:
<221> NAME/KEY: misc_feature
<223> OTHER INFORMATION: n is A, C, G, or T
<220> FEATURE:
<221> NAME/KEY: misc_feature
<222> LOCATION: (13)..(15)
<223> OTHER INFORMATION: n is a, c, g, or t

<400> SEQUENCE: 22
gatcagttgg gtnnncgagt gggttac                                      27

<210> SEQ ID NO 23
<211> LENGTH: 30
<212> TYPE: DNA
<213> ORGANISM: Artificial Sequence
<220> FEATURE:
<223> OTHER INFORMATION: Oligonucleotide for position 104 in the TEM-1
      gene
<220> FEATURE:
<221> NAME/KEY: misc_feature
<223> OTHER INFORMATION: n is A, C, G, or T
<220> FEATURE:
<221> NAME/KEY: misc_feature
<222> LOCATION: (14)..(16)
<223> OTHER INFORMATION: n is a, c, g, or t

<400> SEQUENCE: 23
gaatgacttg gttnnntact caccagtcac                                   30

<210> SEQ ID NO 24
<211> LENGTH: 27
<212> TYPE: DNA
<213> ORGANISM: Artificial Sequence
<220> FEATURE:
<223> OTHER INFORMATION: Oligonucleotide for position 182 in the TEM-1
      gene
<220> FEATURE:
<221> NAME/KEY: misc_feature
<223> OTHER INFORMATION: n is A, C, G, or T
<220> FEATURE:
<221> NAME/KEY: misc_feature
<222> LOCATION: (13)..(15)
<223> OTHER INFORMATION: n is a, c, g, or t

<400> SEQUENCE: 24
cgtgacacca cgnnncctgc agcaatg                                      27

<210> SEQ ID NO 25

```
<211> LENGTH: 27
<212> TYPE: DNA
<213> ORGANISM: Artificial Sequence
<220> FEATURE:
<223> OTHER INFORMATION: Oligonucleotide for position 238 in the TEM-1
      gene
<220> FEATURE:
<221> NAME/KEY: misc_feature
<223> OTHER INFORMATION: n is A, C, G, or T
<220> FEATURE:
<221> NAME/KEY: misc_feature
<222> LOCATION: (13)..(15)
<223> OTHER INFORMATION: n is a, c, g, or t

<400> SEQUENCE: 25
aaatctggag ccnnngagcg tgggtct                                          27
```

METHODS FOR EFFICIENT, EXPANSIVE, USER-DEFINED DNA MUTAGENESIS

CROSS-REFERENCE TO RELATED APPLICATIONS

This application is a 35 U.S.C. §371 U.S. national phase entry of International application No. PCT/US 13/45487 having an international filing date of Jun. 12, 2013, which claims the benefit of U.S. Provisional Application No. 61/658,607, filed Jun. 12, 2012, which are incorporated herein by reference in their entirety.

FEDERALLY SPONSORED RESEARCH OR DEVELOPMENT

This invention was made with government support under DEB-0950939 awarded by the National Science Foundation (NSF). The government has certain rights in the invention.

BACKGROUND

An efficient and high-throughput mutagenesis strategy is an integral part of protein structure/function studies, directed evolution experiments for the discovery of novel proteins, and optimization of genetic elements in synthetic biology systems. Among the methods for in vitro mutagenesis known in the art, none offers a convenient, efficient and high-throughput approach for creating an extensive, user-defined library of variants in which single or multiple mutations can be located at any position. For example, site-directed mutagenesis methods, such as Kunkel mutagenesis (Kunkel, 1985), QuikChange (QuikChange Site-Directed Mutagenesis Kit, Stratagene), and inverse PCR (Dominy and Andrews, 2003), are low-throughput methods. Combined chain reaction requires specially designed sets of primers and cloning of PCR products (Hames et al., 2005; Bi and Stambrook, 1998). Creating mutations by gene synthesis is comparatively expensive and requires sub-cloning of DNA. Error-prone PCR suffers from mutational bias, the inability to define the mutational composition, and the inability to effectively cause most amino acid substitutions, which require two or three mutations in a single codon. Methods that rely on random DNA cleavage reagents or transposons for mutating short sequences of DNA suffer from complex procedures and the inability to target the mutations (Baldwin et al., 2008; Murakami et al., 2002; Liu and Cropp, 2012).

Kunkel mutagenesis is a site-directed method developed to introduce mutations by using a mutation-encoding oligonucleotide (oligo) that anneals to a single-stranded uracil-containing circular DNA template. T7 DNA polymerase and T4 ligase are used to complete synthesis of the mutated strand. Upon transformation of E. coli, the newly synthesized mutated strand survives to a higher extent than the uracil-containing template strand. While the initial Kunkel protocol described making single base substitutions (Kunkel, 1987), other researchers have adapted the method for creating site-saturation libraries in a single codon (Scholle et al., 2005; Weiss et al., 2000). The mutational efficiency of site-directed Kunkel mutagenesis is limited such that typically 50-70% of transformed colonies harbor the desired mutation, while the remainder harbor the wildtype sequence (Kunkel et al., 1987).

Existing methods for site-directed mutagenesis at multiple distal sites simultaneously either have complex and multi-step procedures or have not been demonstrated to be efficient enough for library construction (Bi and Stambrook, 1998; QuikChange Multi Site-Directed Mutagenesis Kit, Stratagene). In addition, the mutagenesis toolbox currently lacks a method for creating extensive DNA libraries with a researcher-defined mutational composition spanning across an entire gene. For example, until now there has been no efficient method to make a library comprising all 18,900 possible single codon substitutions of a 300 amino acid long protein, nor is there an efficient method to make a user-prescribed subset of only 2000 of these 18,900 mutations. Accordingly, current methods to make multiple mutations simultaneously suffer from complicated procedures or low efficiencies and methods for site-directed mutagenesis for creating single mutations suffer from sub-optimal efficiency and variable success.

SUMMARY

In some aspects, the presently disclosed subject matter provides methods for creating one or more user-defined mutations that can be located anywhere in a target sequence, such as in a gene. These mutations can comprise single mutations, multiple mutations, or a comprehensive codon mutagenesis library, in which all possible single codon substitutions in a gene may be created.

In other aspects, the presently disclosed subject matter provides a method for introducing one or more mutations to a single-stranded target nucleic acid molecule, the method comprising: (a) providing a single-stranded uracil-containing template comprising a target nucleic acid molecule in a circular DNA vector; (b) annealing at least one mutagenic oligonucleotide comprising at least one mutation to the target nucleic acid molecule at a first elevated temperature; (c) conducting a first amplification reaction in the presence of a thermostable DNA polymerase and a thermostable DNA ligase at a second elevated temperature to synthesize a mutagenized strand of DNA comprising the at least one mutagenic oligonucleotide; (d) denaturing the mutagenized strand of DNA at a third elevated temperature; (e) annealing a reverse primer to the mutagenized strand of DNA at a fourth elevated temperature; (f) conducting a second amplification reaction in the presence of a thermostable DNA polymerase and a thermostable DNA ligase at a fifth elevated temperature to synthesize a complementary mutant strand of DNA; and (g) degrading the uracil-containing DNA and non-covalently closed circular nucleic acid molecules at a sixth elevated temperature to obtain a mutation-containing double-stranded DNA product.

In further aspects, the presently disclosed subject matter provides a method for introducing one or more mutations to a double-stranded target nucleic acid molecule, the method comprising: (a) providing a double-stranded uracil-containing template comprising a target nucleic acid molecule in a circular DNA vector; (b) denaturing the target nucleic acid molecule at a first elevated temperature; (c) annealing at least one mutagenesis oligonucleotide comprising at least one mutation to the target nucleic acid molecule at a second elevated temperature; (d) conducting a first amplification reaction in the presence of a thermostable DNA polymerase and a thermostable DNA ligase at a third elevated temperature to synthesize a mutagenized strand of DNA comprising the at least one mutagenesis oligonucleotide; (e) degrading the uracil-containing DNA and non-covalently closed circular nucleic acid molecules at a fourth elevated temperature; (f) denaturing the mutagenized strand of DNA at a fifth elevated temperature; (g) annealing a reverse primer to the mutagenized strand of DNA at a sixth elevated temperature;

and (h) conducting a second amplification reaction in the presence of a thermostable DNA polymerase and a thermostable DNA ligase at a seventh elevated temperature to synthesize a complementary mutant strand of DNA to obtain a mutation-containing double-stranded DNA product.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1:
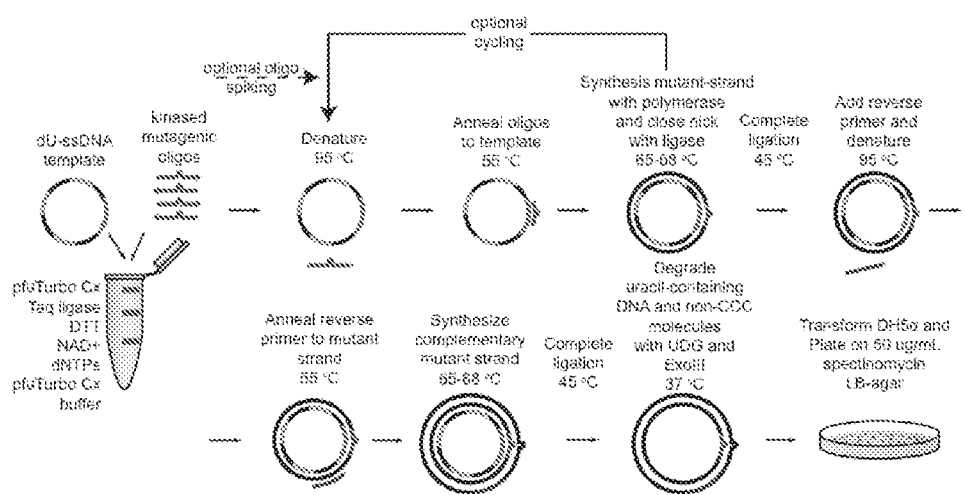
Figure 2:
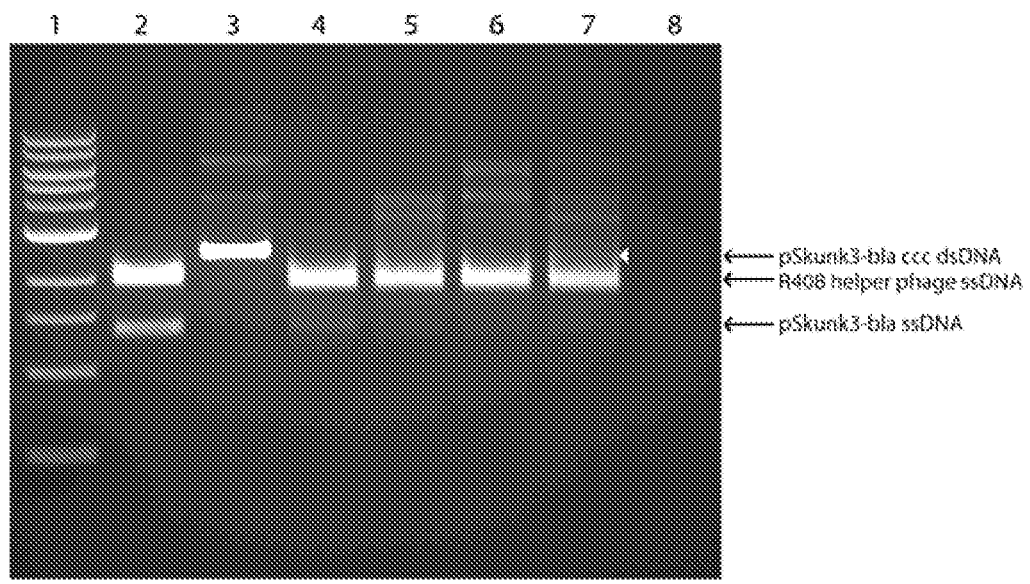
Figure 3:
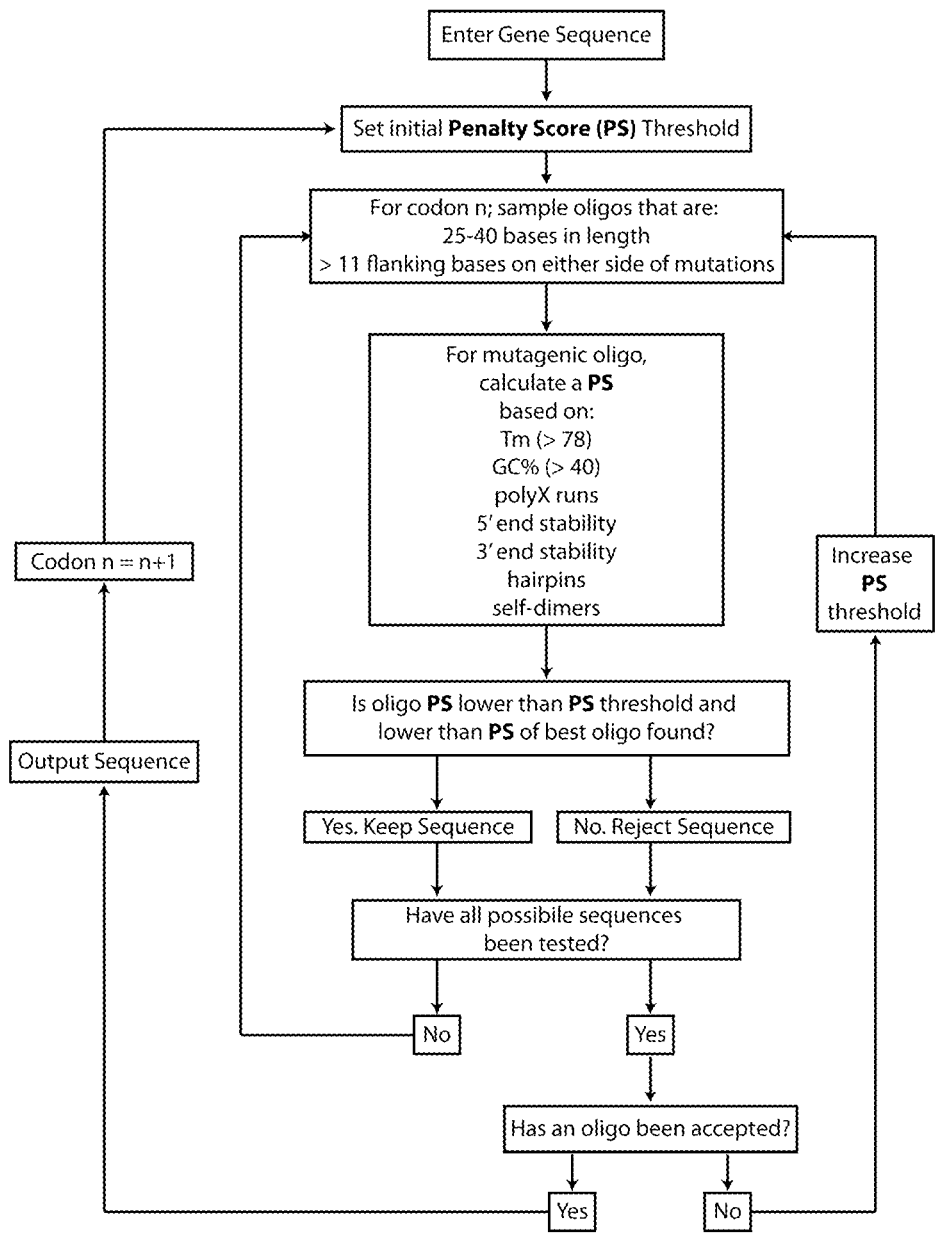
Figure 6:
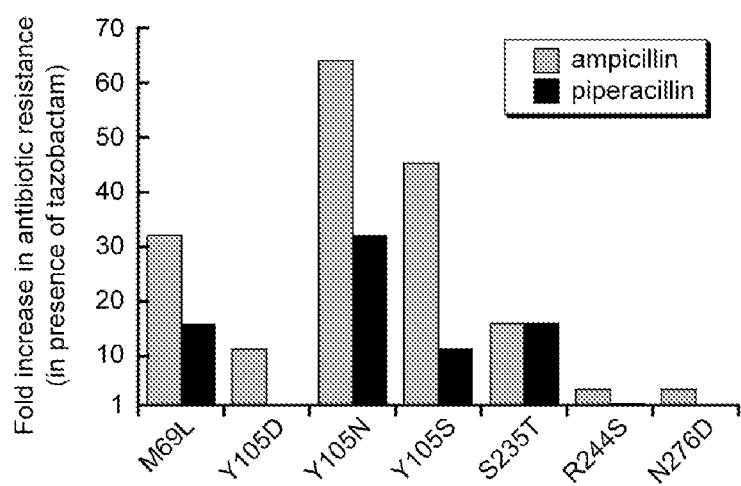
Figure 7:
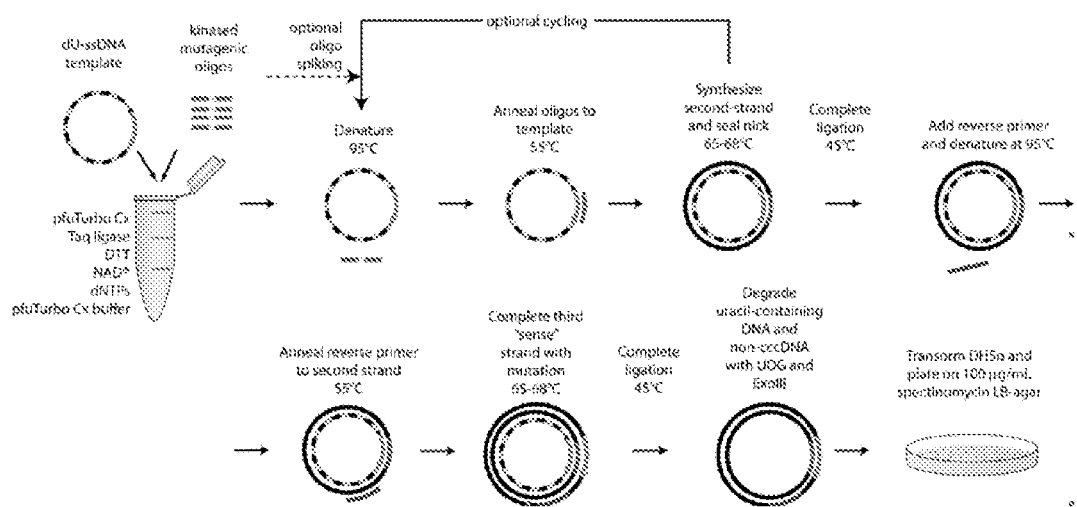

Having thus described the presently disclosed subject matter in general terms, reference will now be made to the accompanying Figures, which are not necessarily drawn to scale, and wherein:

FIG. 1 shows a schematic diagram of PFunkel mutagenesis using a ssDNA template. The basic protocol is depicted. For multiple-site mutagenesis, the addition of the polymerase, dNTPs, ligase, DTT, and NAD+ may be delayed until after the first annealing step. For comprehensive codon mutagenesis, the ratio of oligonucleotide to template is kept low to minimize multiple mutations in a single reaction product. Cycling with occasional spiking of additional mutagenic oligonucleotides improves the reaction yield;

FIG. 2 shows various stages and control reactions for PFunkel site-directed mutagenesis. DNA was visualized on a 1% agarose gel run for 60 min at 75 V. Lane 1:1 kB ladder. Lane 2: uracil-containing ssDNA template prep. Lane 3: pSkunk3-BLA phagemid mini-prep. Lanes 4-6: PFunkel reaction terminated after mutant second strand ligation step. Lane 4: no oligonucleotides added. Lane 5: no ligase added. Lane 6: oligonucleotides and ligase added. Lane 7: PFunkel reaction terminated after third mutagenic strand ligation step. The white triangle indicates the appearance of a band at the correct size to be phagemid cccDNA. Lane 8: The complete reaction prior to transformation;

FIG. 3 shows a schematic diagram of the Matlab algorithm for designing the mutagenic oligonucleotides for comprehensive codon mutagenesis;

FIGS. 4A-4B show completeness and frequency of codon substitutions observed in 454 sequencing of the comprehensive codon mutagenesis library of TEM-1: (a) Number of the 63 possible codon substitutions observed and (b) frequency of codon substitutions observed as a function of position in the gene;

FIGS. 5A-5B show the distribution of the frequency of the type of (a) codon substitutions and (b) codons substituted into the comprehensive codon mutagenesis library CCM-1;

FIG. 6 shows tazobactam resistance of selected alleles. The increase in ampicillin or piperacillin resistance is reported as the fold increase (over TEM-1) in the minimum inhibitory concentration (MIC) of the antibiotic in the presence of 6 μg/mL tazobactam. MIC assays performed in √2-fold increments of antibiotic concentration. Median MIC values of three replicates were used; and FIG. 7 shows a schematic diagram of PFunkel using a dsDNA template.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. PFUNKEL MUTAGENESIS

A. Overview

The presently disclosed subject matter provides versatile and efficient methods for creating user-defined mutations that can be located anywhere in a target sequence. The presently disclosed methods allow for the creation of gene libraries or individual constructs where each member receives one or multiple user-defined mutations at any position.

In some embodiments, the presently disclosed methods allow for a new type of mutagenesis library, a comprehensive codon mutagenesis library, in which all possible single codon substitutions in a gene are created (also termed comprehensive site-saturation mutagenesis). A comprehensive codon mutagenesis library comprises every possible codon substitution in the gene with the goal of only one codon substitution per library member (i.e., library members containing more than one codon mutated are desired to be minimized). Such a library is the equivalent of creating a site-saturation mutagenesis library at all positions in the gene. In other embodiments, the presently disclosed methods can be used to make non-comprehensive libraries, in which not every possible single codon substitution in a gene is created. In some other embodiments, the presently disclosed methods can be used to make non-comprehensive, but extensive libraries, where some, many or most of the possible single codon substitutions in a gene are created.

A significant limitation of Kunkel mutagenesis is the high frequency of wild-type sequences (10-50%) (Kunkel et al., 1987). Without wishing to be bound to any one particular theory, it is postulated that wild-type sequences arise for two reasons. First, the low operating temperature of the second strand synthesis step allows "junk" DNA present in the single stranded DNA prep to prime the single stranded DNA. Such synthesis can either create a wild-type double stranded product or "poison" a mutation-bearing product by creating reaction side-products that possess a nick or a displaced strand (Wassman et al., 2004). Additionally, at lower temperatures, the mutagenic oligonucleotides are more prone to anneal non-specifically to the template. Such reaction side-products that are not in the covalently closed circular DNA (cccDNA) form are prone to degradation by cellular nucleases, removing the mutation. The presence of such junk DNA is apparent from DNA gels of reaction products in which no mutagenic oligonucleotides were added, yet higher molecular weight products are produced (Kunkel et al., 1991). The second postulated reason for the high occurrence of wild-type sequences in Kunkel mutagenesis is the repair of the mutation by mismatch-repair machinery or repair of the uracil-containing template strand in the cell after transformation.

Although there are some similarities between Kunkel mutagenesis and the presently disclosed methods (termed PFunkel mutagenesis), there are a number of key differences that serve to increase the efficiency of the reaction and minimize the appearance of wildtype sequences in the resulting library. At least some of the major differences include, but are not limited to: (a) the use of a thermostable DNA polymerase and ligase, which enables a shift in the operating temperature of the reaction from 25° C.-37° C. to 55° C.-95° C.; (b) the option to use PCR-like thermal cycling and stepwise addition of oligonucleotides to tailor the average number of mutations per gene; (c) synthesis of a second mutated strand complementary to the first mutated strand that displaces the template strand; and (d) in vitro degradation of the uracil-containing template and DNA products not in the desired cccDNA form by the addition of uracil DNA glycosylase (UDG) and an exonuclease, such as exonuclease III (Exo III). Additionally, in some embodiments, PFunkel mutagenesis can be performed on any dsDNA plasmid template and avoids the use of phage.

The in vitro reaction steps of PFunkel mutagenesis (FIG. 1, FIG. 7, Table 4) are designed to eliminate products other than the desired mutated cccDNA plasmid molecules, resulting in high mutational efficiencies. In some embodiments, other than the initial kinase reaction to phosphorylate the mutagenic oligonucleotides, all reaction steps are conveniently performed in the same tube. In other embodiments, no DNA purification is required, except as an optional final step to improve transformation efficiency. In still other embodiments, PFunkel mutagenesis is conveniently performed in a thermocycler.

In some embodiments, the target sequence is a gene. In other embodiments, single mutations can be made using the presently disclosed methods that approach 100% efficiency. In addition, multiple mutations in a target sequence are made at high efficiency. It has been found that increasing the molar ratio of mutagenic oligonucleotide to uracil-containing template increases multiple mutations and decreasing the molar ratio makes only one mutation per molecule more likely. In this way, the number of mutations per molecule can be controlled.

In some embodiments, expansive, user-defined libraries of mutations are created, which comprise some, most, or all possible mutations of a gene or genes or a user-defined subset of all mutations of a gene or genes. As an example of a user-defined subset, comprehensive alanine scanning mutagenesis can be performed using the presently disclosed methods. The ability to make a library comprising all possible mutations of a gene allows the determination of the contribution of each of the residues in a particular protein, for example, to the stability and/or function of the protein. In other embodiments, some, most, or each nucleotide of a target nucleic acid molecule can be substituted to determine the effect on the function of the target nucleic acid molecule. For example, target nucleic acid molecules comprising genes, promoters, enhancers, silencers, insulators, activators, repressors, and the like can be examined by creating a non-comprehensive or comprehensive library of mutations according to the presently disclosed subject matter. Accordingly, in some embodiments, a non-comprehensive or comprehensive codon mutagenesis library is used to obtain an improved protein, gene or gene promoter.

The presently disclosed subject matter can be used to make DNA mutations or DNA mutation libraries with any desired target sequence, such as a gene or genes. The presently disclosed methods also allow the creation of mutations that comprise the deletion or insertion of one or more DNA bases, instead of substitution mutations. The presently disclosed methods allow for introducing one or multiple mutations per variant.

In some embodiments, for making mutations at multiple sites at distant sites in a target sequence simultaneously, the basic PFunkel mutagenesis protocol is modified to increase the frequency of multiple mutations. In some embodiments, the polymerase is added only after the annealing of the mutagenic oligonucleotides. Without wishing to be bound to any one particular theory, the rationale for the delayed addition of polymerase is to prevent a bias for mutations that result from oligonucleotides that anneal efficiently. DNA synthesis from such early annealing oligonucleotides might proceed to regions of the gene where other oligonucleotides are intended to anneal before the oligonucleotides for those locations have a chance to anneal, thus decreasing the frequency of multiple mutations in the resulting transformants. In other embodiments, the extension temperature is reduced from 68° C. to 65° C., to better ensure that the DNA polymerase, such as PfuTurbo Cx, does not strand displace. Strand displacement of a strand created from one mutagenic oligonucleotide by a strand being synthesized starting from a second mutagenic oligonucleotide would also reduce the frequency of multiple mutations.

PFunkel mutagenesis was designed in part to allow efficient construction of libraries in which site-saturation mutagenesis (or any user-defined mutational composition) can be performed at multiple sites simultaneously in a single reaction.

B. Mutagenesis Using a Single-Stranded Template

In some embodiments, the presently disclosed subject matter provides a method for introducing one or more mutations to a single-stranded target nucleic acid molecule, the method comprising: (a) providing a single-stranded uracil-containing template comprising a target nucleic acid molecule in a circular DNA vector; (b) annealing at least one mutagenic oligonucleotide comprising at least one mutation to the target nucleic acid molecule at a first elevated temperature; (c) conducting a first amplification reaction in the presence of a thermostable DNA polymerase and a thermostable DNA ligase at a second elevated temperature to synthesize a mutagenized strand of DNA comprising the at least one mutagenic oligonucleotide; (d) denaturing the mutagenized strand of DNA at a third elevated temperature; (e) annealing a reverse primer to the mutagenized strand of DNA at a fourth elevated temperature; (f) conducting a second amplification reaction in the presence of a thermostable DNA polymerase and a thermostable DNA ligase at a fifth elevated temperature to synthesize a complementary mutant strand of DNA; and (g) degrading the uracil-containing DNA and non-covalently closed circular nucleic acid molecules at a sixth elevated temperature to obtain a mutation-containing double-stranded DNA product.

In some embodiments, the first elevated temperature is from about 50° C. to about 60° C. In other embodiments, the second elevated temperature is from about 60° C. to about 73° C. In still other embodiments, the third elevated temperature is from about 90° C. to about 98° C. In further embodiments, the fourth elevated temperature is about 50° C. to about 60° C. In still further embodiments, the fifth elevated temperature is from about 60° C. to about 73° C. In some embodiments, the sixth elevated temperature is from about 32° C. to about 42° C. In other embodiments, the second elevated temperature and the fifth elevated temperature are about 65° C.

In some embodiments, the presently disclosed methods comprise providing a single-stranded uracil-containing template. In other embodiments, a uracil-containing single-stranded DNA (ssDNA) template containing the gene to be mutated is prepared. In some embodiments, the presently disclosed method comprises producing uracil-containing ssDNA by propagating phagemid DNA comprising the DNA to be mutated in an *E. coli* dut-1 ung-1 host, then infecting the culture with m13 helper phage and harvesting ssDNA from the resulting phage particles. *E. coli* dut-1 ung-1 strains express a heat-sensitive dUTPase that has 5% of wildtype activity at 25° C. but <1% at 37° C., and are deficient in uracil DNA glycosylase activity (Taylor and Weiss, 1982). The result of these mutations is the accumulation of high levels of intracellular dUTP that becomes incorporated in DNA in place of dTTP during DNA synthesis and is not removed due to the lack of UDG activity. In other embodiments, ssDNA preparation takes only a day and requires no special laboratory equipment or highly specialized training (Kunkel et al., 1991). In still other embodiments, the template is prepared by using an m13 helper phage and CJ236, an *E. coli* strain that allows for uracil incorporation into DNA.

In some embodiments, the presently disclosed methods comprise designing mutagenic oligonucleotides. In other embodiments, the mutagenic oligonucleotides are computationally designed. In some other embodiments, the mutagenic oligonucleotide sequences are optimized by using multiple parameters including length, melting temperature, GC content, hairpin and dimer formation, polynucleotide repeats, and hybridization energy. In further embodiments, a single mix of the desired oligonucleotides is synthesized in a high-throughput chip format that allows for up to 3918 different oligonucleotides to be synthesized in parallel. In some embodiments, a mutagenic oligonucleotide encoding a mutation is first 5' phosphorylated in a kinase reaction.

In some embodiments, the target nucleic acid molecule is denatured before annealing at least one mutagenic oligonucleotide to the target nucleic acid molecule. In other embodiments, the target nucleic acid molecule is denatured at a temperature from about 90° C. to about 98° C. In still other embodiments, the target nucleic acid molecule is not denatured before annealing at least one mutagenic oligonucleotide to the target nucleic acid molecule. Without wishing to be bound to any one particular theory, it is though that when high-temperature denaturation of the single-stranded DNA does not occur, the error rate is lowered.

In the annealing step, the oligonucleotides are mixed with the single-stranded template DNA in the presence of a DNA polymerase, DNA ligase and dNTPs. In some embodiments, the DNA polymerase is a thermostable DNA polymerase. In other embodiments, the thermostable DNA polymerase is selected from the group consisting of PfuTurbo Cx DNA polymerase, Taq DNA polymerase, Pfu DNA polymerase, PfuTurbo DNA polymerase, Tma DNA polymerase, Tli DNA polymerase, KOD DNA polymerase, JDF-3 DNA polymerase, PGB-D DNA polymerase, Tgo DNA polymerase, and *Pyrolobus furmarius* DNA polymerase. In a preferred embodiment, the thermostable DNA polymerase is PfuTurbo Cx. In still other embodiments, the DNA ligase is a thermostable DNA ligase. In further embodiments, the thermostable DNA ligase is selected from the group consisting of Pfu DNA ligase, Tth DNA ligase, Taq DNA ligase, *Thermus filiformis* ligase, *Rhodothermus marinus* DNA ligase, *Thermus scotoductus* DNA ligase and *Bacillus stearothermophilus* DNA ligase.

In some embodiments, the annealing step and the synthesizing step occurs at the same time. Therefore, in some embodiments, step (b) and step (c) are performed at the same time. In other embodiments, step (e) and step (f) are performed at the same time.

In some embodiments, the annealing and synthesizing step occurs more than once to produce even more mutation-containing double-stranded DNA product. Therefore, in further embodiments, step (b) and step (c) are performed more than once before step (d) occurs. In still further embodiments, when step (b) and step (c) are performed more than once, at least one additional mutagenic oligonucleotide is added to the reaction in a stepwise manner. In other words, in some embodiments, the incubation temperatures are cycled to perform a denaturing, annealing, extension, and ligation step to complete the mutated second strand and seal the nick. In further embodiments, a second primer that anneals to the new strand outside the gene is added to the reaction, and the denaturing, annealing, extension, and ligation steps are repeated.

In some embodiments, a further step after step (c) and before step (d) comprises completing the ligation at a temperature from about 40° C. to about 50° C. In other embodiments, a further step after step (f) and before step (g) comprises completing the ligation at a temperature from about 40° C. to about 50° C.

In some embodiments, the presently disclosed methods further comprise transforming a host cell with the DNA product from step (g). In other embodiments, the DNA product is purified before being transformed into the host cell. In still other embodiments, the product is transformed into an *E. coli* strain deficient in mismatch repair, which allows the uracil template strand to be degraded and replaced with a new strand containing the desired mutations. In further embodiments, uracil DNA glycosylase and exonuclease III are used to degrade the uracil-containing DNA and non-covalently closed circular nucleic acid molecules. In further embodiments, the *E. coli* strain used is ES1301.

In some embodiments, the mutation-containing double-stranded DNA product comprises one mutation. In other embodiments, when the mutation-containing double-stranded DNA product comprises one mutation, the efficiency of mutagenesis is more than about 70%, such as more than about 75%, more than about 80%, more than about 85%, more than about 90%, more than about 95%, more than about 96%, more than about 97%, more than about 98%, more than about 99%, or about 100%. In some other embodiments, when one mutation is made in the target nucleic acid molecule, the efficiency of mutagenesis is more than about 98%. In further embodiments, when the mutation-containing double-stranded DNA product comprises one mutation, a 4:1 molar ratio of mutagenic oligonucleotide to single-stranded uracil-containing template is used. In still further embodiments, the ratio of mutagenic oligonucleotide to single-stranded uracil-containing template is from about 1:1 to about 100:1.

In some embodiments, the mutation-containing double-stranded DNA product comprises more than one mutation. In other embodiments, when the mutation-containing double-stranded DNA product comprises more than one mutation, the efficiency of mutatgenesis is more than about 60%, such as more than about 70%, more than about 75%, more than about 80%, more than about 85%, more than about 90%, more than about 95%, more than about 96%, more than about 97%, more than about 98%, more than about 99%, or about 100%. In some other embodiments, when more than one mutation is made in the target nucleic acid molecule, the efficiency of mutagenesis is more than about 60%. In some other embodiments, when the mutation-containing double-stranded DNA product comprises more than one mutation, a 1:20 molar ratio of mutagenic oligonucleotide to single-stranded uracil-containing template is used. In further embodiments, the ratio of mutagenic oligonucleotide to single-stranded uracil-containing template is from about 1:1 to about 100:1.

In some embodiments, the mutation-containing double-stranded DNA product comprises a gene. In other embodiments, a non-comprehensive or comprehensive codon mutagenesis library is created.

In some embodiments, at least one mutation is a substitution mutation, a deletion, or an addition of a DNA base or DNA bases.

In some embodiments, to minimize second strand synthesis originating from junk ssDNA annealing to the uracil-containing ssDNA template, the operating temperature is shifted from 25° C.-37° C. (as in the Kunkel method) to 55° C.-95° C. (FIG. 1). This operating temperature requires a high-fidelity thermostable polymerase capable of using a uracil-containing template. Additionally, in some embodiments, a polymerase lacking strand displacement activity is used for creating multiple mutations simultaneously at different sites in a gene. An example of a commercially available polymerase that meets these criteria is PfuTurbo Cx (Agilent Technologies, Santa Clara, Calif., USA), a variant of Pfu polymerase with a V93Q mutation (Nørholm, 2010). This mutation inactivates the uracil-binding pocket of the enzyme that would normally cause it to stall at uracil bases. At less than or equal to 68° C., PfuTurbo Cx does not strand-displace, but still maintains significant polymerase activity (Hogrefe et al., 2001).

After the mutant strand is synthesized, the DNA nick is closed using a ligase. In some embodiments, Taq ligase is chosen due to its effectiveness in ligating DNA nicks, robust activity from 45° C. to 65° C., and ability to withstand many rounds of temperature cycling.

To minimize mismatch repair after transformation, reaction steps were designed to create the desired mutation-containing dsDNA product and degrade non-cccDNA side-products and the uracil-containing template. To create the dsDNA with the designed mutation on both strands, an excess of a 'reverse' oligonucleotide that anneals outside of the gene on the newly created mutant strand can be added, such that it primes synthesis of a new complementary strand that encodes the desired mutations and displaces the uracil-containing template. Treatment with UDG acts to excise the uracil bases from the original template strands leaving apyrimidinic (AP) sites. Treatment with an exonuclease, such as exonuclease III (ExoIII), which has both AP-site endonuclease and 3'->5' exonuclease activity (Rogers and Weiss, 1980), acts to create nicks at the AP sites and then digests the template strand at the nicks and from any 3' end in the context of dsDNA. Therefore, in some embodiments, Exo III and UDG are added to the reaction to remove the template and undesired side-products. In other embodiments, all the steps for this procedure take about three hours to complete.

In some embodiments, the DNA is transformed into *E. coli* without being purified first. In other embodiments, the DNA is purified before being transformed into *E. coli.*

In other embodiments, the mutations are introduced via oligonucleotides that anneal and prime synthesis on a single-stranded uracil-containing DNA template. In other embodiments, the reaction makes use of five enzymes and undergoes multiple temperature cycles that ultimately result in double-stranded closed circular plasmid DNA ready for transformation, each molecule encoding a user-defined mutation.

In further embodiments, the presently disclosed subject matter provides a method for introducing one or more mutations to a single-stranded target nucleic acid molecule, the method comprising: (a) providing a single-stranded uracil-containing template comprising a target nucleic acid molecule in a circular DNA vector; (b) annealing at least one mutagenic oligonucleotide comprising at least one mutation to the target nucleic acid molecule at a first elevated temperature; (c) conducting a first amplification reaction in the presence of a thermostable DNA polymerase and a thermostable DNA ligase at a second elevated temperature to synthesize a mutagenized strand of DNA comprising the at least one mutagenic oligonucleotide; (d) denaturing the mutagenized strand of DNA at a third elevated temperature; (e) annealing a reverse primer to the mutagenized strand of DNA at a fourth elevated temperature; and (f) conducting a second amplification reaction in the presence of a thermostable DNA polymerase and a thermostable DNA ligase at a fifth elevated temperature to synthesize a complementary mutant strand of DNA; (g) degrading the uracil-containing DNA by transforming the products of the second amplification reaction into *E. coli*.

The presently disclosed methods can be optimized for introducing one or more mutations per gene and the frequency of mutated variants can approach 100%. Importantly, the method is rapid, taking a single day and can be performed in a single tube.

C. Mutagenesis Using a Double-Stranded Template (Phage-Less PFunkel Mutagenesis)

The presently disclosed subject methods also can be performed by removing the phage-assisted single-stranded DNA preparation step, to make the method as widely accessible as possible. The methods vary from the methods utilizing a single-stranded template for some of the steps, for example, but the principles of the methods are similar to the principles described hereinabove for a single-stranded template.

This protocol does not require bacteriophage and therefore avoids the need to move the target nucleic acid template from a normal plasmid vector to an appropriate phagemid. In some embodiments, the CJ236 *E. coli* strain is used to prepare the uracil-containing template DNA. In other embodiments, a standard mini-prep procedure is used to obtain the DNA from the *E. coli*.

The protocol used is similar to the PFunkel mutagenesis protocol described hereinabove except for a few minor changes. For example, the dU-single-stranded DNA template is replaced with a dU-double-stranded DNA template. Also, the order of steps is changed such that digestion of the template is performed directly after the first mutant strand is synthesized and ligated. In some embodiments, exonuclease I is added along with exoIII and UDG to improve degradation of the template. The reverse primer step is then performed directly afterwards.

Accordingly, in some embodiments, the presently disclosed subject matter provides a method for introducing one or more mutations to a double-stranded target nucleic acid molecule, the method comprising: (a) providing a double-stranded uracil-containing template comprising a target nucleic acid molecule in a circular DNA vector; (b) denaturing the target nucleic acid molecule at a first elevated temperature; (c) annealing at least one mutagenesis oligonucleotide comprising at least one mutation to the target nucleic acid molecule at a second elevated temperature; (d)

conducting a first amplification reaction in the presence of a thermostable DNA polymerase and a thermostable DNA ligase at a third elevated temperature to synthesize a mutagenized strand of DNA comprising the at least one mutagenesis oligonucleotide; (e) degrading the uracil-containing DNA and non-covalently closed circular nucleic acid molecules at a fourth elevated temperature; (f) denaturing the mutagenized strand of DNA at a fifth elevated temperature; (g) annealing a reverse primer to the mutagenized strand of DNA at a sixth elevated temperature; and (h) conducting a second amplification reaction in the presence of a thermostable DNA polymerase and a thermostable DNA ligase at a seventh elevated temperature to synthesize a complementary mutant strand of DNA to obtain a mutation-containing double-stranded DNA product.

In some embodiments, the first elevated temperature is from about 90° C. to about 98° C. In other embodiments, the second elevated temperature is from about 50° C. to about 60° C. In still other embodiments, the third elevated temperature is from about 60° C. to about 73° C. In further embodiments, the fourth elevated temperature is from about 32° C. to about 42° C. In still further embodiments, the fifth elevated temperature is from about 90° C. to about 98° C. In some embodiments, the sixth elevated temperature is from about 50° C. to about 60° C. In other embodiments, the seventh elevated temperature is from about 60° C. to about 73° C. In some embodiments, the third elevated temperature and the seventh elevated temperature are about 65° C.

The annealing step comprises the use of a DNA polymerase and a DNA ligase. In some embodiments, the DNA polymerase is a thermostable DNA polymerase. In other embodiments, the thermostable DNA polymerase is selected from the group consisting of PfuTurbo Cx DNA polymerase, Taq DNA polymerase, Pfu DNA polymerase, PfuTurbo DNA polymerase, Tma DNA polymerase, Tli DNA polymerase, KOD DNA polymerase, JDF-3 DNA polymerase, PGB-D DNA polymerase, Tgo DNA polymerase and *Pyrolobus furmarius* DNA polymerase. In a preferred embodiment, the thermostable DNA polymerase is Pfu-Turbo Cx. In some other embodiments, the DNA ligase is a thermostable DNA ligase. In further embodiments, the thermostable DNA ligase is selected from the group consisting of Pfu DNA ligase, Tth DNA ligase, Taq DNA ligase, *Thermus filiformis* ligase, *Rhodothermus marinus* DNA ligase, *Thermus scotoductus* DNA ligase and *Bacillus stearothermophilus* DNA ligase.

In some embodiments, step (c) and step (d) are performed at the same time. In other embodiments, step (g) and step (h) are performed at the same time.

In some embodiments, step (c) and step (d) are performed more than once before step (e) occurs. In other embodiments, when step (c) and step (d) are performed more than once, at least one additional mutagenic oligonucleotide is added to the reaction in a stepwise manner.

In further embodiments, uracil DNA glycosylase and exonuclease III are used to degrade the uracil-containing DNA and non-covalently closed circular nucleic acid molecules after the first amplification reaction occurs.

In some embodiments, a further step after step (d) and before step (e) comprises completing the ligation at a temperature from about 40° C. to about 50° C. In other embodiments, a further step after step (h) comprises completing the ligation at a temperature from about 40° C. to about 50° C.

In some embodiments, the mutation-containing double-stranded DNA product comprises one mutation. In other embodiments, the efficiency of mutagenesis is more than about 98%. In still other embodiments, a 4:1 molar ratio of mutagenic oligonucleotide to double-stranded uracil-containing template is used. In further embodiments, the ratio of mutagenic oligonucleotide to double-stranded uracil-containing template is from about 1:1 to about 100:1.

In some embodiments, the mutation-containing double-stranded DNA product comprises more than one mutation.

In some embodiments, the mutation-containing double-stranded DNA product comprises a gene. In other embodiments, a non-comprehensive or comprehensive codon mutagenesis library is created.

In some embodiments, at least one mutation is a substitution mutation, a deletion, or an addition of a DNA base.

In some embodiments, the presently disclosed methods further comprise transforming a host cell with the DNA product from step (h). In other embodiments, the DNA product is purified before being transformed into the host cell.

D. Comprehensive or Non-Comprehensive Codon Mutagenesis Libraries

The presently disclosed methods allow the creation of a new type of mutagenesis library, a comprehensive codon mutagenesis library, in which all possible single codon substitutions in a gene are created (this can also be called comprehensive site-saturation mutagenesis). A comprehensive codon mutagenesis library comprises every possible codon substitution in the gene with only one codon substitution per library member (i.e., library members containing more than one codon mutated are desired to be minimized). Such a library is the equivalent of creating a site-saturation mutagenesis library at all positions in the gene.

The presently disclosed methods also allow the creation of a non-comprehensive codon mutagenesis library. By "non-comprehensive", it is meant that the mutation-containing double-stranded DNA products from the presently disclosed methods do not encompass all possible mutation-containing double-stranded DNA products in a particular reaction, but comprise some, many, or most of the possible mutation-containing double-stranded DNA products in a particular reaction. Therefore, a non-comprehensive codon mutagenesis library comprises some, many, or most of every possible codon substitution in a gene.

The presently disclosed methods can be efficiently used to make a library of the desired single mutations when performing the reaction at low molar ratio of oligonucleotide to DNA template. Increasing the ratio allows one to make libraries comprising mutants with two or more of the oligonucleotide-prescribed mutations. As the ratio of oligonucleotide to DNA template is increased, the distribution of multiple mutations will increase. In some embodiments, increasing the ratio of oligonucleotide to DNA template will move the distribution from 1, 2, 3, 4, etc. mutations per target nucleic acid molecule (template), for example, to 2, 3, 4, 5., etc. mutations per target nucleic acid molecule. The number of mutations made per target nucleic acid molecule and the number of target nucleic acid molecules with that number of mutations depends on the ratio of oligonucleotide to DNA template. Therefore, the molar ratio of oligonucleotide to DNA template can be varied using the presently disclosed methods to control the number of mutations made in a DNA template. As is known in the art, the actual amount of oligonucleotide desired in the reaction will depend on the nucleic acid sequence of the template and oligonucleotide, the volume of the reaction, the buffers used, the amount of time the reaction is allowed to proceed, and the like.

The ability of the presently disclosed methods to access mutations (and combinations of mutations) effectively inaccessible by the current state of the art should be useful for many fields, such as for the directed evolution of proteins. Furthermore, the ability to custom tailor the set of mutations facilitates constructing focused libraries computationally enriched for mutants with improved function.

The presently disclosed methods utilizing a single-stranded target DNA molecule were used to create a comprehensive codon mutagenesis library of the TEM-1 β-lactamase gene (described herein below). This library was designed to contain 18,081 members, one for each possible codon substitution in the gene (287 positions in TEM-1×63 possible codon substitutions). Deep sequencing revealed that approximately 97% of the designed single codon substitutions are present in the library. Non-comprehensive or comprehensive codon mutagenesis libraries can be created using both single-stranded and double-stranded DNA molecules.

D. Kits for Performing PFunkel Mutagenesis

The presently disclosed subject matter also relates to kits for practicing the methods of the presently disclosed subject matter. In general, a presently disclosed kit contains some or all of the components, reagents, supplies, and the like to practice a method according to the presently disclosed subject matter. In some embodiments, the term "kit" refers to any intended any article of manufacture (e.g., a package or a container) comprising an oligonucleotide and a set of particular instructions for practicing the methods of the presently disclosed subject matter. In other embodiments, the kit comprises a thermostable DNA polymerase and DNA ligase along with a set of particular instructions for practicing the methods of the presently disclosed subject matter. The kit typically comprises an effective amount of reagents to perform at least one mutagenesis reaction.

In some embodiments, the presently disclosed subject matter provides a kit comprising a set of instructions for performing the presently disclosed methods. In other embodiments, the kit further comprises a thermostable DNA ligase, a thermostable DNA polymerase, and/or an oligonucleotide.

II. DEFINITIONS

The term "nucleic acid molecule" is used broadly herein to mean a sequence of deoxyribonucleotides or ribonucleotides that are linked together by a phosphodiester bond. "Nucleic acid molecule" is meant to include DNA and RNA, which can be single stranded or double stranded, as well as DNA/RNA hybrids. Furthermore, the term "nucleic acid molecule" as used herein includes naturally occurring nucleic acid molecules, which can be isolated from a cell, for example, a particular gene of interest, as well as synthetic molecules, which can be prepared, for example, by methods of chemical synthesis or by enzymatic methods such as by the polymerase chain reaction (PCR), and, in various embodiments, can contain nucleotide analogs or a backbone bond other than a phosphodiester bond.

The terms "polynucleotide" and "oligonucleotide" also are used herein to refer to nucleic acid molecules. Although no specific distinction from each other or from "nucleic acid molecule" is intended by the use of these terms, the term "polynucleotide" is used generally in reference to a nucleic acid molecule that encodes a polypeptide, or a peptide portion thereof, whereas the term "oligonucleotide" is used generally in reference to a nucleotide sequence useful as a probe, a PCR primer, an antisense molecule, or the like. Of course, it will be recognized that an "oligonucleotide" also can encode a peptide. As such, the different terms are used primarily for convenience of discussion.

A polynucleotide or oligonucleotide comprising naturally occurring nucleotides and phosphodiester bonds can be chemically synthesized or can be produced using recombinant DNA methods, using an appropriate polynucleotide as a template. In comparison, a polynucleotide comprising nucleotide analogs or covalent bonds other than phosphodiester bonds generally will be chemically synthesized, although an enzyme such as T7 polymerase can incorporate certain types of nucleotide analogs into a polynucleotide and, therefore, can be used to produce such a polynucleotide recombinantly from an appropriate template.

The terms "target nucleic acid molecule" or "target DNA molecule" are used herein to refer to the nucleic acid or DNA sequence that is mutagenized using the presently disclosed methods.

The term "mutation" is used herein to refer to an alteration in a polynucleotide sequence. A mutation according to the presently disclosed subject matter can involve substitution, insertion or deletion. A polynucleotide in which a mutation has occurred is called a "mutant". Mutation may be introduced to one or both strands of a double-stranded polynucleotide. The strand of a double-stranded polynucleotide in which a mutation has occurred is referred to as a "mutant strand"; the strand with no mutation introduced is called a "non-mutant strand". The term "mutagenesis" according to the invention refers to the introduction of mutations into a polynucleotide sequence. Mutations are preferably introduced into a target DNA molecule using one or more mutagenic primers in an amplification reaction. During the amplification reaction, multiple copies of the strand complementary to the target DNA strand are synthesized by incorporating the mutagenic primer and extending the incorporated primer using the target strand as a template.

The term "introducing one or more mutations to a single-stranded target nucleic acid molecule" or "introducing one or more mutations to a double-stranded target nucleic acid molecule" refers to introducing the one or more mutations into the same copy of the complementary strand synthesized during the amplification reaction. In addition, "introducing one or more mutations" may also refer to introducing one or more mutations into two or more different copies of the complementary strands synthesized during the amplification reaction.

The term "substitution" refers to a replacement of one or more nucleotides by different nucleotides. "Insertion" refers to a change in nucleotide sequence wherein one or more nucleotides have been added. "Deletion" refers to a change in nucleotide sequence wherein one or more nucleotides are removed.

The term "primer" refers to a polynucleotide, i.e., a purified restriction fragment or a synthetic polynucleotide, that is capable of acting as a point of initiation of synthesis when placed under conditions in which synthesis of a primer extension product complementary to a polynucleotide strand (the "template") is induced, i.e., in the presence of nucleotides and an agent for polymerization such as DNA polymerase and at a suitable temperature and pH.

The term "mutagenic oligonucleotide" or "mutagenic primer" or "primer" refers to an oligonucleotide used in an amplification reaction, wherein the oligonucleotide does not precisely match the target hybridization sequence (e.g., the sequence of a target nucleic acid molecule). The mismatched nucleotides in the mutagenic oligonucleotide are referred to as "mutation site" or "site" with respect to the target sequence (e.g., the sequence of a target DNA molecule). Thus, during the amplification reaction, the mismatched nucleotides of the oligonucleotide are incorporated into the amplified product thereby resulting in the synthesis of a mutant DNA strand comprising the mutagenic oligonucleotide that was used to prime synthesis of the target sequence. A mutagenic oligonucleotide, according to the presently disclosed subject matter, is complementary to one strand of a target nucleic acid molecule and contains at least 50%, and preferably at least 75%, at least 90% of the nucleotide residues capable of base pairing with a target nucleic acid molecule (e.g., a target DNA molecule).

A "mutagenic oligonucleotide" of the presently disclosed subject matter, also refers to a "degenerate oligonucleotide". As used herein, a "degenerate oligonucleotide" is a primer mixture synthesized with mixed bases where there is more than one nucleotide sequence possibility for at least one codon coding for an amino acid. An amino acid is coded by three sequential nucleotides (a codon) in a polynucleotide sequence, more than one codon can encode for the same amino acid. A "degenerate oligonucleotide" according to the presently disclosed subject matter may comprise one or more degenerated codon sequences.

"Complementary" as used herein refers to the broad concept of sequence complementarity between regions of two polynucleotide strands or between two regions of the same polynucleotide strand. It is known that an adenine residue of a first polynucleotide region is capable of forming specific hydrogen bonds ("base pairing") with a residue of a second polynucleotide region which is antiparallel to the first region if the residue is thymine or uracil. Similarly, it is known that a cytosine residue of a first polynucleotide strand is capable of base pairing with a residue of a second polynucleotide strand which is antiparallel to the first strand if the residue is guanine. A first region of a polynucleotide is complementary to a second region of the same or a different polynucleotide if, when the two regions are arranged in an antiparallel fashion, at least one nucleotide residue of the first region is capable of base pairing with a residue of the second region. A first polynucleotide that is 100% complementary to a second polynucleotide forms a base pair at every nucleotide position. A first polynucleotide that is not 100% complementary (e.g., 90%, or 80% or 70% complementary) contains mismatched nucleotides at one or more nucleotide positions.

"Annealing" as used herein refers to the formation of a double-stranded polynucleotide between two separate single strands sufficient to prime DNA synthesis in an amplification reaction. "Annealing" occurs through complementary base pairing between the two separated strands, which are at least 50% or more (e.g., 60%, 70%, 80%, 90%, 95% or more) complementary to each other.

"Amplification" as used herein refers to any in vitro method for synthesizing one or both strands of a polynucleotide template sequence (e.g., a target nucleic acid molecule) with the use of a polymerase. Polynucleotide amplification results in the incorporation of nucleotides into a polynucleotide (e.g., DNA) molecule or primer thereby forming a new polynucleotide molecule complementary to the polynucleotide template. The formed polynucleotide molecule and its template can be used as templates to synthesize additional polynucleotide molecules. As used herein, one amplification reaction may comprise many cycles of polynucleotide synthesis. Amplification reactions include the polymerase chain reaction, ligase chain reaction (LCR), and polynucleotide sequence based amplification, for example.

"Polymerase chain reaction" or "PCR" refers to an in vitro method for amplifying a specific polynucleotide template sequence. The PCR reaction involves a repetitive series of temperature cycles. The reaction mix comprises dNTPs (each of the four deoxynucleotides dATP, dCTP, dGTP, and dTTP), primers, buffers, DNA polymerase, and target nucleic acid molecule or template.

"A mutation-containing double-stranded DNA product" or "a mutation-containing single-stranded DNA product" refers to the double strand and/or single strand polynucleotide population generated with a mutagenic oligonucleotide during or at the end of an amplification reaction. The amplified product, according to the presently disclosed methods, contains mutations to the original target nucleic acid molecule due to the incorporation of mutagenic primers in the amplification reaction.

"Thermostable" as used herein refers to an enzyme which is stable to heat, is heat resistant, and functions at high temperatures, e.g., 50° C. to 90° C. Thermostable enzymes are usually purified from the hyperthermophiles of archaebacteria, which grow optimally at temperatures around 100° C.

"Ligating" or "ligation" as used herein refers to covalently attaching polynucleotide sequences together to form a single sequence. This is typically performed by treatment with a ligase which catalyzes the formation of a phosphodiester bond between the 5' end of one sequence and the 3' end of the other. The ligase catalyses the formation of a phosphodiester bond at the site of a single-stranded break in duplex DNA.

"Mutational efficiency" as used herein refers to the percentage of polynucleotide which has incorporated at least one mutagenic primer used in the amplification reaction.

"Host cell" refers to a cell that comprises a recombinant polynucleotide molecule, typically a recombinant plasmid or other expression vector. Thus, for example, host cells can express genes that are not found within the native (non-recombinant) form of the cell. The host cell may be prokaryotic or eukaryotic, including bacterial, mammalian, yeast, *aspergillus*, and insect cells.

The term "transform" as used herein refers to a process of introducing one or more exogenous DNA molecules into a host cell and/or the expression of the DNA molecules in the host cell. A host cell with one or more exogenous DNA molecules is a transformant.

"Elevated temperature" as used herein refers to a temperature above room temperature. Generally, "elevated temperature" refers to a temperature from about 30° C. to above 100° C.

"Degrading" a molecule as used herein refers to breaking down the molecule. For example, uracil-containing DNA can be degraded when transformed into a host cell.

The terms "promoter", "promoter region" or "promoter sequence" refer generally to transcriptional regulatory regions of a gene, which may be found at the 5' or 3' side of the coding region, or within the coding region, or within introns. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site as well as protein binding domains (consensus sequences) responsible for the binding of RNA polymerase.

Unless defined otherwise, all technical and scientific terms used herein have the meaning commonly understood by a person skilled in the art to which this invention belongs.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Methods and Materials

Materials

All enzymes were obtained from New England Biolabs (NEB; Ipswich, Mass., USA) except PfuTurbo Cx Hotstart DNA polymerase, which was obtained from Agilent Technologies (Santa Clara, Calif., USA). *E. coli* strain CJ236 and NEB 5-alpha F'I$^q$ competent cells were obtained from NEB (Ipswich, Mass., USA) and strain DH5α was obtained from Invitrogen (Carlsbad, Calif., USA). R408 helper phage was obtained from Promega (Fitchburg, Wis., USA). All oligonucleotides were ordered from Integrated DNA Technologies (Coralville, Iowa, USA). For the construction of library CCM-1 (machine-mixed degenerate oligonucleotides), oligonucleotides were ordered in 96-well format at the 10 nmol synthesis scale such that each oligonucleotide was provided at a concentration of 100 μM in DI water. For the construction of library CCM-2 (hand-mixed degenerate oligonucleotides), oligonucleotides were ordered in 96-well format at the 100 nmole synthesis scale such that each oligonucleotide was provided at a concentration of 100 μM in DI water. The secondary oligonucleotide P320, P-gcagaaattcgaaagcaaattcgac (SEQ ID No: 1), was ordered with 5' phosphorylation. All other chemical reagents were obtained from Sigma-Aldrich (St. Louis, Mo., USA).

Preparation of CJ236 Competent Cells

*E. coli* strain CJ236 was plated on LB-agar plates with 15 μg/mL chloramphenicol (Cm), 125 μg/mL deoxythymidine (dThd) and grown at 30° C. Although it is usual to proceed with competent cell preparation from a single colony (especially if using a new cell stock validated by the manufacturer), the desired strain phenotype was first confirmed as an optional step. A colony with the proper temperature-sensitive dut-1 phenotype was identified by replica plating on M9 minimal media agar (Sambrook et al., 2001) supplemented with and without 125 μg/mL dThd and incubated at 30° C. and 42° C. for approximately 40 hours. A colony was selected which displayed the desired phenotype of stunted growth at 42° C., which was improved with dThd. This colony was used to prepare chemically competent cells (Chung et al., 1989). To prevent genetic drift and reversal of the dut-1 ung-1 phenotype, it is best to propagate CJ236 at 30° C. or lower in deoxythymidine (dThd) supplemented media. These conditions reduce uracil incorporation in DNA (an unfavorable mutagenic event leading to reversions of this phenotype) since uracil incorporation is unnecessary when propagating the strain. However, during preparation of uracil-containing ssDNA or dsDNA template, the strain was grown at 37° C. without dThd for increased uracil incorporation.

Preparation of Uracil-Containing ssDNA Template pSkunk3-BLA is a 4.4 kB phagemid derived from pDIM-C8-BLA (Sohka et al., 2009) in which the coding sequence of the Cm resistance gene was replaced with the streptomycin/spectinomycin (Sm/Spec) resistance gene. This phagemid was used to transform CJ236 cells which were then plated on LB-agar with 50 μg/mL Spec, 15 μg/mL Cm, and 125 μg/mL dThd and incubated overnight at 30° C. A single colony was used to inoculate 10 mL of LB supplemented with Cm, Spec, and dThd as above, which was incubated with shaking at 30° C. overnight. The cell density of the culture was determined from the $OD_{600nm}$ using the correlation $2 \times 10^8$ CFU/mL·$OD_{600nm}$. In a 20 mL test tube, 2 mL of TBG media (Trower, 1994) with 50 μg/mL Spec was inoculated with $2 \times 10^7$ CFU from the overnight culture and $1 \times 10^8$ pfu R408 helper phage for a multiplicity of infection (MOI) of 5. This culture was incubated for 6 hours at 37° C. with shaking at 300 rpm. The culture was then centrifuged for 5 minutes at 16,100×g to pellet the cells, and the phage-containing supernatant recovered. Then 300 μL of 2.5 M NaCl/20% PEG was added to the supernatant and the mixture was incubated at 4° C. for 1 hour to precipitate the phage. The phage was pelleted by centrifugation at 20,817×g for 10 minutes at 4° C. The liquid supernatant was discarded and the phage pellet resuspended in 150 μL PBS. The Qiagen QIAprep Spin M13 kit (#27704; Hilden, Germany) was then used to purify ssDNA from the phage as per the manufacturer's directions. The absorbance at 260 nm of the ssDNA sample was measured using a Nanodrop ND-1000 spectrophotometer (Thermo Fisher Scientific, Waltham, Mass., USA) and converted to a concentration using the relation 1.0 $A_{260nm}$=33 μg/μL.

Site-Directed PFunkel Mutagenesis Using a ssDNA Template

All steps were performed in a pre-programmed Eppendorf Mastercycler personal thermocycler (Eppendorf, Hamburg, Germany). A mutagenic oligonucleotide (5'-gacaccacgatgcatgcagcaatggc; SEQ ID No: 2) encoding a c542a mutation in the bla gene was phosphorylated in a 50 μL reaction containing 1X T4 PNK buffer, 1 mM ATP, 5 mM DTT, 3.0 μM oligonucleotide and 10 units T4 PNK. The reaction was incubated at 37° C. for 1 hour, and the enzyme inactivated at 65° C. for 20 minutes.

The PFunkel reaction was prepared in a 0.5 mL eppendorf tube containing 1X pfuTurbo Cx hotstart DNA polymerase buffer, 10 mM DTT, 0.5 mM NAD+, 0.2 mM dNTPs, 1 μL of the kinase reaction, 1 μg (0.75 pmol) of dU-ssDNA template, 2.5 units PfuTurbo Cx hotstart DNA polymerase, and 200 cohesive end units Taq ligase in a total volume of 100 μL. The free Mg2+ concentration should be maintained between 0.5-2.5 mM since low concentration reduces polymerase fidelity while high concentration leads to nonspecific annealing of oligonucleotides (PfuTurbo Cx hotstart DNA polymerase Instruction Manual, 2009). The volume of kinase reaction added should therefore be minimized to maintain Mg2+ concentration in the mutagenesis reaction close to the 2 mM Mg2+ provided in the 1X polymerase buffer.

The following denaturation/annealing/extension/ligation steps were performed: 95° C. for 3 min, 55° C. for 90 sec, 68° C. for 15 min and 45° C. for 15 min. Then 3.8 pmol of oligonucleotide P320 (5'-P-gcagaaattcgaaagcaaattcgac; SEQ ID No: 1) was added and one more cycle of 95° C. for 30 sec, 55° C. for 45 sec, 68° C. for 10 min and 45° C. for 15 mins was performed. Then 10 units of UDG and 30 units of ExoIII were added and incubated at 37° C. for 1 hr followed by an inactivation step at 70° C. for 20 min.

Five μL of the unpurified reaction was used to directly transform 100 μL of DH5α chemically competent cells (Chung et al., 1989). The entire transformation was plated on an LB-agar plate with 50 μg/mL Spec and incubated overnight at 37° C. To obtain more transformants, the remaining DNA was then purified using the Zymo DNA Clean & Concentrator kit (Zymo Research Corporation, Irvine, Calif., USA) according to the manufacturer's instructions and eluted in 15 μL of 1X EB. One μL was electroporated into 50 μL DH5α electrocompetent cells and then incubated with SOC recovery media for 1 hr at 37° C. with shaking at 250 rpm. The transformation was plated on LB-agar with 50 μg/mL Spec and incubated overnight at 37° C.

For the experiments of Table 2, the reaction was scaled down to 200 ng template and 20 μL volume.

Multi-Site PFunkel Mutagenesis Using a ssDNA Template

Four oligonucleotides were designed to introduce NNN random bases at codon positions 42, 104, 182, and 238 in the bla gene with respective sequences: 5'-gatcagttgggtnnnc-gagtgggttac (SEQ ID No: 3), 5'-gaatgacttggttnnntactcacca-gtcac (SEQ ID No: 4), 5'-cgtgacaccacgnnncctgcagcaatg (SEQ ID No. 5), 5'-aaatctggagccnnngagcgtgggtct (SEQ ID No. 6). These oligos were combined in equimolar amounts and phosphorylated in a 50 μL reaction containing 1X T4 PNK buffer, 1 mM ATP, 5 mM DTT, 6.0 μM total oligonucleotide and 10 units T4 PNK. The reaction was incubated at 37° C. for 1 hour, and the enzyme inactivated at 65° C. for 20 minutes.

The annealing reaction was prepared in a 0.5 mL eppendorf tube containing 1X pfuTurbo Cx hotstart DNA polymerase buffer, 2 μL of kinase reaction, and 1 μg of pSkunk3-bla ssDNA template in a total volume of 77 μL. The annealing was performed by heating to 95° C. for 3 min, then 55° C. for 10 min, and holding at 55° C.

Meanwhile, in a separate PCR tube, 1X PfuTurbo Cx hotstart DNA polymerase buffer and 2.75 units of PfuTurbo Cx hotstart DNA polymerase were combined in a total volume of 5.5 μL. The hotstart polymerase was heat activated by heating to 95° C. for 3 min.

After the annealing step, 10 mM DTT, 1 mM NAD+, 0.2 mM dNTPs, 5 μL of the activated polymerase solution, and 200 cohesive end units Taq ligase was added bringing the total volume to 100 μL. The reaction was mixed by slowly and gently pipetting up and down. Extension and ligation of the mutant strand was performed at 65° C. for 15 min and 45° C. for 15 min. Five units of UDG and 2 units of ExoIII were added and the mixture was incubated at 37° C. for 1 hr followed by an inactivation step at 70° C. for 20 min. A total of 3.8 pmol of oligonucleotide P320 was added and one more cycle of 95° C. for 30 sec, 55° C. for 45 sec, 68° C. for 10 min and 45° C. for 15 mins was performed. The DNA was purified using the Zymo DNA Clean & Concentrator kit (Zymo Research Corporation, Irvine, Calif., USA) according to the manufacturer's instructions and eluted in 15 μL of DI water. This solution was vacuum concentrated down to 1-2 μL, electroporated into 50 μL DH5α electrocompetent cells and then incubated with SOC recovery media for 1 hr at 37° C. with shaking at 250 rpm. The transformation was plated on LB-agar with 50 μg/mL Spec and incubated overnight at 37° C.

For the experiments of Table 2, the reaction was scaled down to 200 ng template and 20 μL volume.

Comprehensive Codon Mutagenesis by PFunkel Using a ssDNA Template

All steps were performed in a pre-programmed Eppendorf Mastercycler personal thermocycler. Equimolar amounts of 287 different mutagenic oligos were combined in a single tube at a total oligonucleotide concentration of 100 μM. The oligonucleotides were phosphorylated in a 50 μL reaction containing 1X T4 PNK buffer, 1 mM ATP, 5 mM DTT, 0.038 μM oligonucleotides and 10 units T4 PNK. The reaction was incubated at 37° C. for 1 hour, and the enzyme inactivated at 65° C. for 20 minutes.

The PFunkel reaction was prepared in a 0.5 mL eppendorf tube containing 1X PfuTurbo Cx hotstart DNA polymerase buffer, 10 mM DTT, 0.5 mM NAD+, 0.2 mM dNTPs, 1 μL of the kinase reaction, 1 μg (0.75 pmol) of dU-ssDNA template, 2.5 units PfuTurbo Cx hotstart DNA polymerase, and 200 cohesive end units Taq ligase in a total volume of 100 μL. The following denaturation/annealing/extension steps were performed: 95° C. for 2 min, 15 cycles of 95° C. for 30 sec, 55° C. for 45 sec, and 68° C. for 6.5 min. At the 95° C. step of cycles 6 and 11, 1 μL of the kinase reaction was added and mixed in by stirring with the pipette tip. The reaction was then incubated at 45° C. for 15 min for ligation to occur. Then 3.8 pmol of oligonucleotide P320 (5:1 molar ratio oligonucleotide to template) was added and one more cycle of 95° C. for 30 sec, 55° C. for 45 sec, and 68° C. for 10 min was carried out. The reaction was again incubated at 45° C. for 15 min. Then 10 units of UDG and 30 units of ExoIII were added and incubated at 37° C. for 1 hr followed by an inactivation step at 70° C. for 20 min. The DNA was then purified using the Zymo DNA Clean & Concentrator kit (Zymo Research Corporation, Irvine, Calif., USA) according to the manufacturer's instructions and eluted in 15 µL of DI water. This volume was then vacuum concentrated down to 1-2 µL. For CCM-1, the DNA was electroporated into 50 µL DH5α electrocompetent cells and then incubated with SOC recovery media for 1 hr at 37° C. with shaking at 250 rpm. The entire volume was then plated on a Nalgene Bioassay dish (D4803; 245 mm×245 mm×25 mm) containing LB-agar with 50 µg/mL Spec and incubated overnight at 37° C. For CCM-2, the DNA was used to transform NEB 5-alpha F'Iq competent cells as per the manufacturer's instructions, and then plated on a Nalgene Bioassay dish containing LBagar with 50 µg/mL Spec, 15 µg/mL tetracycline, and 2 w/v % glucose.

Reaction Conditions for the PFunkel Mutagenesis Using a ssDNA Template

Table 1 shows representative embodiments of reaction conditions for the PFunkel mutagenesis using a single-stranded DNA template.

created using Titanium Lib-A fusion primers that included a 10-base MID barcode. Each 25 µL PCR reaction had 1-2 ng linearized template DNA, 0.4 µM each primer, 200 µM each dNTP, 1X HF Phusion buffer, and 2 units Phusion high-fidelity polymerase. Cycler conditions were 98° C. for 30 sec, 30 cycles of 98° C. for 30 sec, 55° C. for 30 sec, 72° C. for 30 sec, and then 72° C. for 5 min. PCR products were visualized on an ethidium bromide 1% agarose gel, and then gel purified using the QIAquick Gel Extraction Kit (28706). Amplicons were furthered purified using the Agencourt AMPure XP PCR Purification kit (A63880; Beckman Coulter, Brea, Calif., USA), to remove short DNA fragments, primers, and primer dimers. DNA concentration was determined using the Quant-iT Picogreen dsDNA Assay kit (P7589; Life Technologies, Carlsbad, Calif., USA). Amplicons from each sub-library were diluted to 1E9 molecules/µL in 1X TE, equal volumes pooled together and then further diluted to 1E7 molecules/µL in DI water. 454 sequencing was performed by Tufts University Core Facility on a Roche

TABLE 1

Reaction conditions for PFunkel using a ssDNA template.

|  | Site-directed mutagenesis | Multiple-site mutagenesis | Comprehensive codon mutagenesis |
|---|---|---|---|
| Start with | PfuTurbo Cx buffer<br>2.5 units PfuTurbo Cx polymerase<br>10 mM DTT<br>0.5 mM NAD$^+$<br>0.2 mM dNTPs<br>1 µg (0.75 pmol) of dU-ssDNA<br>1 µL of 3 µM kinased mutagenic oligo<br>200 cohesive end units Taq ligase<br>100 µL total volume | PfuTurbo Cx buffer<br>1 µg (0.75 pmol) of dU-ssDNA<br>2 µL of 6 µM kinased mutagenic oligo mixture<br>77 µL total volume | PfuTurbo Cx buffer<br>2.5 units PfuTurbo Cx polymerase<br>10 mM DTT<br>0.5 mM NAD$^+$<br>0.2 mM dNTPs<br>1 µg (0.75 pmol) of dU-ssDNA<br>1 µL of 0.038 µM kinased mutagenic oligo mix<br>200 cohesive end units Taq ligase<br>100 µL total volume |
| Initial step | none | None | 95° C. for 2 min. |
| Cycling | 1 cycle of<br>95° C. for 3 min<br>55° C. for 90 sec<br>68° C. for 15 min | 95° C. for 3 min,<br>55° C. for 10 min<br>hold at 55° C.<br>add<br>10 mM DTT<br>0.5 mM NAD$^+$<br>0.2 mM dNTPs<br>2.5 units PfuTurbo Cx (previously heat activated)<br>200 cohesive end units Taq ligase<br>bringing the total volume to 100 µL<br>65° C. for 15 min | 15 cycles of<br>95° C. for 30 sec<br>55° C. for 45 sec<br>68° C. for 6.5 min.<br>At the 95° C. step of cycles 6 and 11, an additional 1 µL of the kinase reaction was added. |
| Ligation | 45° C. for 15 min | | |
| add Synthesis of second strand containing mutation | Add 3.8 pmol of kinased oligo P320 (5:1 molar ratio oligo to template)<br>one cycle of<br>95° C. for 30 sec<br>55° C. for 45 sec<br>68° C. for 10 min<br>45° C. for 15 min (ligation) | | |
| Degradation of template and side-products | Shift to 37° C.<br>Add 10 units of UDG + 30 units of ExoIII; incubate 1 hour at 37° C.; 70° C. for 20 min (heat inactivation) | Shift to 37° C.<br>Add 5 units of UDG + 2 units of ExoIII; incubate 30 min at 37° C.; 70° C. for 20 min (heat inactivation) | Shift to 37° C.<br>Add 10 units of UDG + 30 units of ExoIII; incubate 1 hour at 37° C.; 70° C. for 20 min (heat inactivation) |
| Final step | Purify DNA (optional step to increase number of transformants) and transform | | |

454 GS FLX High-Throughput Sequencing

Transformants were recovered from agar plates with LB broth, and plasmid DNA recovered using the Qiagen QIAprep Spin Miniprep kit (27106). The plasmid DNA was linearized by restriction endonuclease digestion with NdeI. PCR amplicons of each of the three bla libraries were created using Titanium Lib-A fusion primers that included a 454 GS FLX+ instrument (Basel, Switzerland). The sequencing data was then analyzed using the Galaxy open web-based platform (Goecks et al., 2010; Blankenberg et al., 2010; Giardine et al., 2005) and custom Matlab scripts.

Identification of Adaptive Codon Substitutions for Tazobactam Resistance in TEM-1

Library CCM-2 was plated at a density of about 500 CFU/cm² (non-selective conditions) on LB-agar plates supplemented with 50 µg/mL Spec, 300 µM IPTG, 100 µg/mL ampicillin and 4 µg/mL or 6 µg/mL tazobactam. Plates were incubated at 37° C. for 17 hours. The tazobactam concentration chosen was 1.3 or 2-fold higher than the concentration at which cells bearing wildtype TEM-1 could grow effectively. Large colonies on the plates were chosen at random for sequencing.

Selected single base mutations were re-introduced into TEM-1 by site-directed PFunkel mutagenesis on the 20 µL volume scale. The MIC for ampicillin and piperacillin of the mutants was assessed with and without 6 µg/mL tazobactam by spotting 104 CFU on Mueller-Hinton agar plates containing 50 µg/mL Spec, 300 µM IPTG, and √2-fold increments of either ampicillin or piperacillin. Plates were incubated at 37° C. for 12 hrs.

Preparation of Uracil-Containing dsDNA Template for Phage-Less PFunkel

A 10 mL LB culture of CJ236 cells with the pSkunk3-bla plasmid was incubated overnight at 37° C. with shaking at 250 rpm. Plasmid dU-dsDNA was then isolated using the Qiagen QIAprep Spin Miniprep kit (#27106; Qiagen, Hilden, Germany) and the concentration quantified using a Nanodrop ND-1000 spectrophotometer (Thermo Fisher Scientific, Waltham, Mass., USA).

Site-Directed PFunkel Mutagenesis Using a Plasmid dsDNA Template

All steps were performed in a pre-programmed Eppendorf Mastercycler personal thermocycler (Eppendorf, Hamburg, Germany). A mutagenic oligo (5'-gacaccacgatgcatgcagcaatggc) encoding a c542a mutation in TEM-1 was phosphorylated in a 50 µL reaction containing 1X T4 PNK buffer, 1 mM ATP, 5 mM DTT, 1.5 µM oligo and 10 units T4 PNK. The reaction was incubated at 37° C. for 1 hour and the enzyme inactivated at 65° C. for 20 minutes.

The PFunkel reaction was prepared in a 0.5 mL tube containing 1X PfuTurbo Cx hotstart DNA polymerase buffer, 10 mM DTT, 0.5 mM NAD+, 0.2 mM dNTPs, 1 µL of the kinase reaction, 1 µg (0.38 pmol) of dU-dsDNA template, 2.5 units PfuTurbo Cx hotstart DNA polymerase, and 200 cohesive end units Taq ligase in a total volume of 100 µL. The free Mg2+ concentration should be maintained between 0.5-2.5 mM since low concentration reduces polymerase fidelity while high concentration leads to nonspecific annealing of oligos (PfuTurbo Cx hotstart DNA Polymerase Instruction Manual, 2009). The volume of kinase reaction added should therefore be minimized to maintain Mg2+ concentration in the mutagenesis reaction close to the 2 mM Mg2+ provided in the 1X polymerase buffer. The following denaturation/annealing/extension/ligation steps were performed: 95° C. for 3 min, 55° C. for 90 sec, 68° C. for 15 min and 45° C. for 15 min. Next, 10 units of UDG and 30 units of Exo III were added and the reaction was incubated at 37° C. for 1 hr followed by an inactivation step at 70° C. for 20 min. A total of 3.8 pmol of oligo P320 (5'-Pgcagaaat-tcgaaagcaaattcgac; SEQ ID No: 1) was added and one more cycle of 95° C. for 30 sec, 55° C. for 45 sec, 68° C. for 10 min and 45° C. for 15 min was performed. The DNA was purified using the Zymo DNA Clean & Concentrator kit (Zymo Research Corporation, Irvine, Calif., USA) according to the manufacturer's instructions and eluted in 15 µL of DI water. This solution was vacuum concentrated down to 1-2 µL, electroporated into 50 µL DH5α electrocompetent cells, which were incubated with SOC recovery media for 1 hr at 37° C. with shaking at 250 rpm. The transformation was plated on LB-agar with 50 µg/mL Spec and incubated overnight at 37° C.

Multi-Site PFunkel Mutagenesis Using a Plasmid dsDNA Template

Four oligos were designed to introduce the four mutations A42G, E104K, M182T, and G238S in the bla gene with respective sequences: 5'-gatcagttgggtgga cgagtgggttac (SEQ ID No: 7), 5'-ctcagaatgacttggttaagtactcaccagtcacag (SEQ ID No: 8), 5'-gtgacaccacgacgcctgcagcaatggcaacaac (SEQ ID No: 9), 5'-gctgataaatctggagccagtgagcgtgggtctcg (SEQ ID No: 10). These oligos were combined in equimolar amounts and phosphorylated in a 50 µL reaction containing 1X T4 PNK buffer, 1 mM ATP, 5 mM DTT, 3 µM total oligo and 10 units T4 PNK. The reaction was incubated at 37° C. for 1 hour and the enzyme inactivated at 65° C. for 20 minutes.

The annealing reaction was prepared in a 0.5 mL eppendorf tube containing 1X PfuTurbo Cx hotstart DNA polymerase buffer, 2 µL of kinase reaction, and 1 µg of dUds-DNA template in a total volume of 77 µL. The annealing was performed by heating to 95° C. for 3 min, then 55° C. for 10 min, and holding at 55° C.

Meanwhile, in a separate PCR tube, 1X PfuTurbo Cx hotstart DNA polymerase buffer and 2.75 units of PfuTurbo Cx hotstart DNA polymerase polymerase were combined in a total volume of 5.5 µL. The hotstart polymerase was heat activated by heating to 95° C. for 3 min.

After the annealing step, 10 mM DTT, 0.5 mM NAD+, 0.2 mM dNTPs, 5 µL of the activated polymerase solution, and 200 cohesive end units Taq ligase was added bringing the total volume to 100 µL. The reaction was mixed by slowly and gently pipetting up and down. Extension and ligation of the mutant strand was performed at 65° C. for 15 min and 45° C. for 15 min. Five units of UDG and 2 units of ExoIII were added and the mixture was incubated at 37° C. for 1 hr followed by an inactivation step at 70° C. for 20 min. A total of 3.8 pmol of oligo P320 was added and one more cycle of 95° C. for 30 sec, 55° C. for 45 sec, 68° C. for 10 min and 45° C. for 15 min was performed. The DNA was purified using the Zymo DNA Clean & Concentrator kit (Zymo Research Corporation, Irvine, Calif., USA) according to the manufacturer's instructions and eluted in 15 µL of DI water. This solution was vacuum concentrated down to 1 µL-2 µL, electroporated into 50 µL DH5α electrocompetent cells and then incubated with SOC recovery media for 1 hr at 37° C. with shaking at 250 rpm. The transformation was plated on LB-agar with 50 µg/mL Spec and incubated overnight at 37° C.

Example 2

Site-Directed PFunkel Mutagenesis

A mutagenic oligonucleotide encoding a c542a (P183H in the protein) mutation in the TEM-1 β-lactamase (TEM-1) gene was first 5' phosphorylated in a kinase reaction. The phosphorylated oligonucleotide was then combined with the ssDNA uracil-containing template in molar ratio of 4:1 together with the polymerase and ligase. The incubation temperatures were cycled to perform a denaturing, annealing, extension, and ligation step to complete the mutated second strand and seal the nick. A second primer that annealed to the new strand outside the gene was added to the reaction, and the denaturing, annealing, extension, and ligation steps were repeated. Exo III and UDG were then added to the reaction to remove the template and undesired side-products. All steps for this procedure took about 3 hrs to complete.

A DNA gel showing steps in the reaction and various control reactions is shown in FIG. 2. The white triangle indicates the appearance of a band at the correct size to be phagemid cccDNA. Without being bound to any one particular theory, it is believed that the amount of cccDNA product in the complete reaction prior to transformation (lane 8) is too low to visualize.

A transformation of 5 µL of the unpurified reaction with 100 µL of chemically competent cells yielded over 1000 transformants, illustrating that, in some embodiments, DNA purification is not necessary when using the presently disclosed methods. The remaining DNA was purified using a spin column and 1/15th of the product was electroporated into electrocompetent DH5α E. coli yielding 533,000 transformants Sequencing of the TEM-1 gene from 23 colonies showed that all 23 (100%) contained the c542a mutation encoded by the oligonucleotide. No undesired mutations were
observed. The high mutational efficiency of the presently disclosed methods was further substantiated using eleven different oligonucleotides encoding either a 1 or 2 base substitution at different locations of the gene (Table 2).

TABLE 2

Results of additional testing of PFunkel site-directed mutagenesis and multi-site mutagenesis using a single-stranded DNA template.

| Type of PFunkel | Oligonucleotides added in reaction[a] Mutation(s) Intended | Number of correct sequences[b] |
|---|---|---|
| Site-directed Mutagenesis | M69L | 2 of 2 |
| | Y105S | 2 of 2 |
| | Y105D | 2 of 2[e] |
| | Y105N | 2 of 2 |
| | S235T | 2 of 2 |
| | R244S | 2 of 2 |
| | N276D | 2 of 2 |
| | A42G | 2 of 2 |
| | E104K | 2 of 2[d] |
| | M182Q | 2 of 2 |
| | G238A | 2 of 2 |
| Multisite Mutagenesis | A42G, E104K | 2 of 2 |
| | A42G, M182Q | 2 of 2 |
| | A42G, G238A | 2 of 2 |
| | E104K, M182Q | 2 of 2 |
| | E104K, G238A | 1 of 2 |
| | M182Q, G238A | 1 of 2 |
| | A42G, E104K, M182Q | 1 of 2 |
| | A42G, E104K, G238A | 1 of 2 |
| | A42G, M182Q, G238A | 1 of 2 |

TABLE 2-continued

Results of additional testing of PFunkel site-directed mutagenesis and multi-site mutagenesis using a single-stranded DNA template.

| Type of PFunkel | Oligonucleotides added in reaction[a] Mutation(s) Intended | Number of correct sequences[b] |
|---|---|---|
| | E104K, M182Q, G238A | 1 of 2 |
| | A42G, E104K, M182Q, G238A | 2 of 2 |

[a]M69L encodes atg69ctg (5' - cccgaagaacgttttccaatgctgagcactttaaa-3'; SEQ ID No: 11)
Y105S encodes tac105tcc (5' - tgacttggttgagtcctcaccagtcacaga-3'; SEQ ID No: 12)
Y105D encodes tac105gac (5' - tgacttggttgaggactcaccagtcacaga-3'; SEQ ID No: 13)
Y105N encodes tac105aac (5' - tgacttggttgagaactcaccagtcacaga-3'; SEQ ID No: 14)
S235T encodes tct235act (5' - attgctgataaaactggagccggtgagc-3'; SEQ ID No: 15)
R244S encodes cgc244agc (5' - gagcgtgggtctagcggtatcattgca-3'; SEQ ID No: 16)
N276D encodes aat276gat (5' - atggatgaacgagatagacagatcgctgaga-3'; SEQ ID No: 17)
A42G encodes gca42ggg (5' - gatcagttgggtgggcgagtgggttac-3'; SEQ ID No: 18)
E104K encodes gag104aag (5' - ctcagaatgacttggttaagtactcaccagtcacag-3'; SEQ ID No: 19)
M182Q encodes atg182cag (5' - cgtgacaccacgcagcctgcagcaatg-3'; SEQ ID No: 20)
G238A encodes ggt238gca (5' - aaatctggagccgcagagcgtgggtct-3'; SEQ ID No: 21)
[b]The number of clones with all intended mutations out of the total number of clones sequenced.
[c]One clone had an additional, unintended point mutation.
[d]One clone had an additional, unintended mutation found near the desired mutation, presumably resulting from the synthesized mutagenic oligo possessing a misincorporated base.

Example 3

Multi-Site PFunkel Mutagenesis

To demonstrate multiple-site mutagenesis using PFunkel mutagenesis, four mutagenic oligonucleotides designed to create site-saturation libraries of four codons in different regions of the TEM-1 gene simultaneously were synthesized. The oligonucleotides encoding NNN at codon positions A42, E104, M182, and G238 were combined with the ssDNA template such that each oligonucleotide was present in an oligonucleotide to template molar ratio of 4:1. Electroporation of the entire reaction product after spin column purification yielded 5.8 million transformants. Sequencing of the TEM-1 gene of 10 colonies showed that 7 variants had mutations at all 4 designated codon positions, 2 had mutations at 3 positions, and 1 had mutations at 2 positions (Table 3). Twenty-nine of the 35 codon substitutions were unique and no undesired mutations were observed. Multi-site PFunkel was further substantiated by constructing 11 different double, triple, or quadruple mutants at 73% efficiency (Table 2). The error rate for single or multi-site PFunkel mutagenesis was approximately $5 \times 10^{-5}$, higher than expected based on the error rate of PfuTurbo Cx in a PCR reaction.

TABLE 3

Mutations in 10 clones of the naïve multi-site library

| | Ambler Position[a] | | | | | | | |
|---|---|---|---|---|---|---|---|---|
| | 42 | | 104 | | 182 | | 238 | |
| Colony | Codon | Amino Acid | Codon | Amino Acid | Codon | Amino Acid | Codon | Amino Acid |
| TEM-1 | gca | A | gag | E | atg | M | ggt | G |
| 1 | ggc | G | — | — | cag | Q | tgg | W |

TABLE 3-continued

Mutations in 10 clones of the naïve multi-site library

| | Ambler Position[a] | | | | | | | |
|---|---|---|---|---|---|---|---|---|
| | 42 | | 104 | | 182 | | 238 | |
| Colony | Codon | Amino Acid | Codon | Amino Acid | Codon | Amino Acid | Codon | Amino Acid |
| 2 | agc | S | ggg | G | gga | G | — | — |
| 3 | cgg | R | ggg | G | cgg | R | aga | R |
| 4 | tgc | C | ggg | G | agg | R | cgg | R |
| 5 | tgc | C | gcg | A | ggg | G | gtg | V |
| 6 | ggc | G | tgg | W | ccg | P | ctg | L |
| 7 | ggc | G | ggg | G | ttg | L | gac | D |
| 8 | ggt | G | ggg | G | gca | A | atc | I |
| 9 | gcg | A | ggt | G | cat | H | atc | I |
| 10 | — | — | — | — | — | — | tcc | S |

[a] oligo for position 42: 5'- gatcagttgggtnnncgagtgggttac-3'; SEQ ID No: 22
oligo for position 104: 5'- gaatgacttggttnnntactcaccagtcac-3'; SEQ ID No: 23
oligo for position 182: 5'- cgtgacaccacgnnncctgcagcaatg-3'; SEQ ID No: 24
oligo for position 238: 5'- aaatctggagccnnngagcgtgggtct-3'; SEQ ID No: 25

Example 4

Comprehensive Codon Mutagenesis

The presently disclosed methods were used to create a library designed to encompass all possible single codon substitutions in the TEM-1 gene (287 codons×63 possible codon substitutions at each codon=18,081 desired mutants). In this example, it was not desired to create a library with more than one codon substituted. Such a library is the equivalent of performing site-saturation mutagenesis at all positions in the gene simultaneously. At least one advantage of the presently disclosed methods is that one does not have to perform 287 separate mutagenesis reactions or 287 separate gene syntheses to create this library. The library would also be much closer to a true random mutagenesis library than one created by error prone PCR, which is biased towards certain base substitutions made by the polymerase and certain amino acid substitutions accomplished by single base mutations.

The 287 degenerate mutagenic oligonucleotides (one for each of the 287 codons to be mutated) were designed in silico using a Matlab script or algorithm (FIG. 3). For each gene position to be randomized, the algorithm scans through many possible oligonucleotides, assigns each a score based on specific guidelines, and then selects the best scoring oligonucleotide sequence. Published design criteria (QuikChange Site-Directed Mutagenesis Kit, Instruction Manual) along with early experimental data were used to develop the following oligonucleotide criteria: (a) the oligonucleotide length can vary from 27 to 40 bases; (b) the mismatched bases must be flanked by greater than or equal to 12 bases on each side; (c) the Tm must be greater than or equal to 62° C.; (d) the GC content must be greater than or equal to 40%; (e) oligonucleotides with a stable 5' end and an unstable 3' end are favored to prevent non-specific annealing and extension; and (f) oligonucleotides with polynucleotide repeats, hairpin structures, and a propensity for dimerization are penalized. Each oligonucleotide is designed to replace a different codon in the bla gene with a random sequence (NNN). The script can be easily modified for designing other types of libraries.

The oligonucleotides were purchased in desalted 96-well format using machine-mixed degenerate bases and pooled. To minimize the occurrence of multiple mutations, the total oligonucleotide to ssDNA template ratio was kept low (1:20), which makes two oligonucleotides annealing to the same ssDNA template unlikely. To increase the yield and efficiency of the reaction, a cycling reaction of denaturing, annealing, and extension was implemented to allow multiple chances for each oligonucleotide to productively anneal. Fifteen cycles were performed with additional oligonucleotides spiked in at the 6th and 11th cycle. Additional cycles and oligonucleotide additions can be performed if larger libraries are desired. Without wishing to be bound to any one particular theory, the presently disclosed methods are analogous to that of a discontinuous fed batch reactor—a reaction strategy to minimize undesirable side products that occur with a high concentration of one of the reactants (Denbigh, 1944).

In some embodiments, the library can be created in a single tube. In this example, the library was divided into thirds corresponding to each ⅓ of the gene to facilitate characterization of the library by 454-GS-FLX Titanium sequencing, which has a read length of approximately 400 bp for the sequencing of amplicons from pools of DNA. Transformation of the entire reaction product yielded approximately 500,000 transformants for each library.

Sequencing of 30 members of each library indicated that the libraries mostly consisted of single codon substitutions (87%) with the remainder being wildtype (13%) (Table 4). No clones with multiple mutations were observed. Two of the sequences contained a single mutation outside the region subjected to mutagenesis, which was attributed to polymerase error. It was postulated that additional rounds of cycling and mutagenic oligonucleotide addition would lower the fraction of wild-type sequences closer to the theoretical minimum of 1.6% (i.e., 1/64 of the NNN containing oligonucleotides encode the wildtype codon). These three libraries collectively were named CCM-1.

Figure 4:
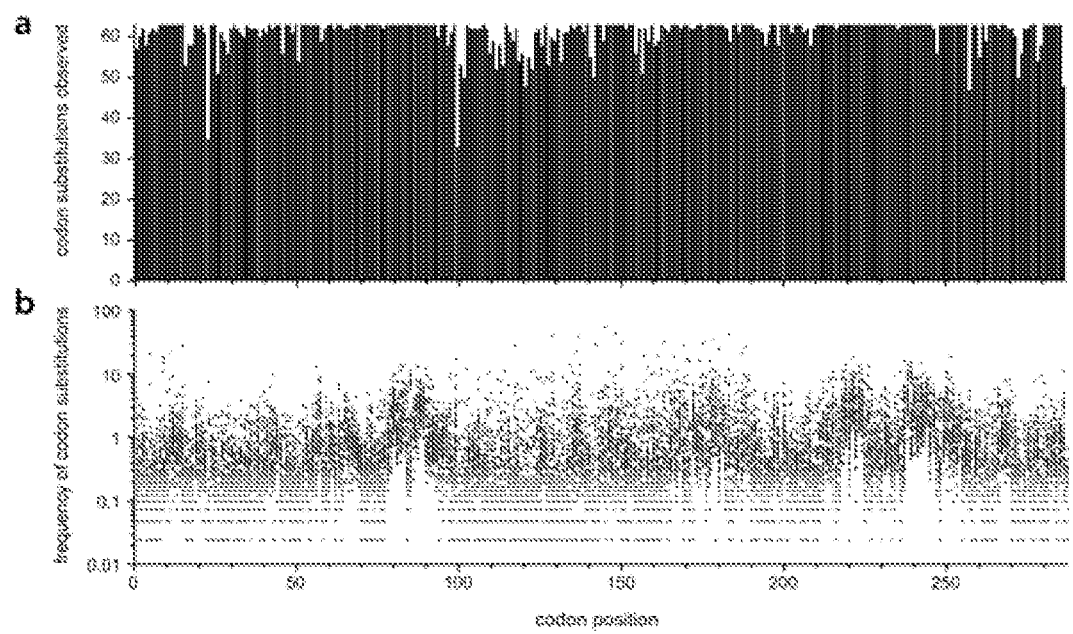

The CCM-1 library was extensively analyzed using 454-GS-FLX Titanium sequencing. FIG. 4 shows the frequency of each of the 63 possible codon substitutions for each of the 287 codons of TEM-1, except for the 3% of the 18,081 codon substitutions that were not observed. The frequency is based on 454 sequencing in which 738,615 codon substitutions were observed in 787,488 reads. The frequency is normalized to the frequency that would occur if all substitutions were evenly distributed among the 18,081 possible substitutions (i.e., frequency=1.0 means that the substitution was observed 738,615/18,081=41 times). The number of codon substitutions observed resulting from sequencing errors is small (approximately 4% of the 738,615 codon substitutions observed).

The analysis indicated that 96-97% of the 18,081 desired codon substitutions were present in the library and greater than or equal to 97% of library members with a codon substitution contained only one codon substitution (Table 5, described herein below). The frequency of codon substitutions observed as a function of gene position showed that a few positions were hotspots for substitutions and that the frequency of codon substitutions had a broad distribution (FIG. 4). Without wishing to be bound to any one particular theory, it is believed that the occurrence of hotspots reflected the suitably of the respective oligonucleotides for this mutagenesis technique. Codon substitutions with a single base pair change were observed at about twice the expected frequency, and this came at the expense of fewer codon substitutions with three base pair changes (Table 4). Without wishing to be bound to any one particular theory, it is believed that a portion of the bias towards single base substitutions was likely due to polymerase errors during library construction, polymerase errors during the PCR-based amplicon preparation for sequencing, and 454 sequencing errors, all of which would be primarily single base substitutions. The remainder of the bias may reflect the increased mismatch between the mutagenic oligonucleotide and the template for codon substitutions with three mutated bases. Still, although codon substitutions with three base pair changes may have been somewhat disfavored, 95% of the 7749 designed 3-base pair change codon substitutions in the 454 sequencing results were observed (Table 4). Since 454 sequencing errors with three base pair changes in a codon are likely very rare, it is believed most if not all of these 3-base substitutions were present in the library.

454 GS FLX High-Throughput Sequencing Analysis of the Comprehensive Codon Substitution Library Barcoded amplicons from the three CCM-1 libraries were created by PCR and pooled. Additionally, barcoded amplicons created from the wildtype TEM-1 gene were added to the pool as a control for sequencing errors. 787,488 reads that passed quality filtering were obtained, with a median length of 354 bases. A total of 99% of the reads spanned the entire mutated region of the amplicon. The reads of the library DNA displayed a higher frequency of both wildtype (26%) and multiple mutations (17%) at the expense of single codon mutations (57%) as compared to the Sanger sequencing of 90 clones. However, this was determined to be an artifact of the amplicon preparation known as "PCR jumping," a well-documented occurrence during PCR amplification of highly-identical, heterogeneous template sequences in which chimera PCR products are produced (Holland et al., 2011; Meyerhans et al., 1990). This was confirmed to be the case by Sanger sequencing of 28 individual PCR amplicons of which 36% had no mutations, 50% had one codon mutation, and 14% had multiple codon mutations (Table 4). This closely matched the proportions in the 454 sequencing. The sequencing of wild-type TEM-1 indicated that the sequencing error rate (0.035 codon substitutions per read) was much less than the frequency of codon substitutions observed in the reads of the library DNA (0.94 per read). It was concluded that 96% of the codon substitutions observed in the 454 sequencing reads were present in the library, with the remainder being sequencing errors. Of the codon substitutions present in the library, less than or equal to 3% were present in library members with multiple mutations (based on Sanger sequencing). In the 454 sequencing reads of the library, 97.0% of the 18,081 intended codon substitutions were observed at least once. In the worst-case scenario, in which sequencing errors are assigned to mutations with the lowest numbers of occurrences, 84.8% of the 18,081 possible mutants were present in the library. If sequencing errors are evenly distributed across all codon substitutions, 96.4% were present. In the best-case scenario, in which errors are assigned to mutants that are highly represented, 96.8% of the 18,081 mutants were present. It is believed that the true coverage of the library lies between 96.4% and 97% and likely closer to 97%, since 454 sequencing is known to exhibit sequence-dependent common errors. Among the 72 sequencing errors in the reads of wild-type TEM-1, one particular substitution appeared five times and five codon substitutions appeared twice. More extensive sequencing of wild-type TEM-1 would be necessary to accurately determine the frequency at which each of the 18,081 possible codon substitutions appear because of sequencing error, and thus the true frequency of each codon substitution in the library.

Both the Sanger and the 454 sequencing indicate that G's are present in mutated codons 2.3 times more frequently than any one of the other three bases (Table 5). The high frequency of G's is also apparent in the sequences of naïve members of the multi-site mutagenesis library (Table 3), which used four specific primers from the set of 287. The distribution of the frequency of the substituted codons strongly reflects this bias (FIG. 5A) whereas the distribution of the frequency of codons substituted into does not (FIG. 5B). Since TEM-1 has roughly an equal frequency of all bases, it is concluded that this bias results from a 2.3-fold bias for incorporation of G's during the synthesis of the machine-mixed degenerate oligonucleotides. This bias contributed to the underrepresentation of certain mutations, as the frequency of G's in codon substitutions not observed in the 454 sequencing was 0.068. The frequency is normalized to that expected if all codon substitutions occurred with equal frequency. The codon substitutions are color coded as to the number of G's in the substituted codon. TEM-1 lacks three codons (TAG, TGA, AGG) so those codons are not included in the codons substituted into.

TABLE 4

Statistics of comprehensive codon mutagenesis library CCM-1.

| | Expected in an ideal library | Sequencing of individual clones of the library | Sequencing of PCR amplicons used in 454 sequencing | 454 sequencing of the library | 454 sequencing of TEM-1 |
|---|---|---|---|---|---|
| Sequences | | 90 clones | 28 clones | 787,488 reads | 2040 reads |
| Percent of reads that cover entire gene segment | | 100% | 100% | 98.95% | 99.75% |
| Number of mutated codons in all sequences | | 78 + 2[a] | 22 | 738,615 | 72 |
| Mean mutated codons per sequence | 0.9844 | 0.87 | 0.79 | 0.94 | 0.035 |
| Percent of clones/reads with | | | | | |
| No mutations | 1.56% | 13.33% | 35.71% | 26.17%[b] | 96.9% |
| One mutation | 98.44% | 86.67% | 50.00 | 56.71% | 2.75% |
| Multiple mutations | 0.00% | 0.00% | 14.29% | 17.12% | 0.034% |
| Percent of mutated codons with | | | | | |
| 1 base substitution | 14.29% | 22.50% | 22.72% | 31.97% | 86.11% |
| 2 base substitution | 42.86% | 47.50% | 59.10% | 41.84% | 13.89% |
| 3 base substitution | 42.86% | 30.00% | 18.18% | 26.20% | 0.00% |
| Percent of possible codon substitutions observed | | | | | |
| 1 base substitution | | | | 99.96% | |
| 2 base substitutions | | | | 97.70% | |
| 3 base substitutions | | | | 95.33% | |
| All substitutions | | | | 97.01% | |

[a] two mutations were identified outside the region targeted for mutagenesis
[b] most of the reads with multiple mutations and about 50% of the reads with no mutations result from PCR jumping during amplicon creation (see text hereinbelow).

The library mostly is comprised of members with one mutation as indicated in sequencing of individual clones.

TABLE 5

Percent of bases in mutated codons in the comprehensive codon mutagenesis library CCM-1.

| Base | Expected in an ideal library | Sequencing of 90 individual clones of the library | 454 sequencing of library | 454 sequencing of TEM-1 (i.e. sequencing errors) |
|---|---|---|---|---|
| G | 25.00% | 46.25% | 43.26% | 26.85% |
| A | 25.00% | 17.08% | 18.84% | 18.52% |
| T | 25.00% | 18.33% | 18.81% | 24.54% |
| C | 25.00% | 18.33% | 19.09% | 30.09% |

Construction and Characterization of Comprehensive Codon Mutagenesis Library CCM-2

To confirm that the bias for G's resulted from their overrepresentation in the mutagenic oligonucleotides, a second set of three libraries (CCM-2) was constructed using a second set of degenerate mutagenic oligonucleotides that were synthesized using a hand-mixed ratio of bases (instead of machine mixed). The three libraries were transformed into NEB 5-alpha F'Iq cells, which contain the lacIq repressor to better repress expression to avoid any bias when propagating the library. Sequencing of 30 members of each library revealed 8.9% wildtype, 83.1% single codon substitutions in the targeted region, 1.1% with a single mutation outside the targeted region, and 6.7% multiple mutations (3 of 6 had two-mutations in the targeted region; 3 of 6 had one codon substitution in the targeted region and the second mutation in a non-targeted region). The frequency of bases substituted in the designed mutations of CCM-2 (27.5%: 26.6%:23.0%:23.0% for G:A:C:T) was much more even than in CCM-1. The ratio of 1-base: 2-base: 3-base substitutions in the targeted region was 7.7%: 42.2%: 30.1%.

PFunkel Error Rate

PfuTurbo Cx hotstart DNA polymerase has a published error rate of $1.3 \times 10^{-6}$ in a PCR reaction using a double-stranded template (PfuTurbo Cx Hotstart DNA Polymerase Instruction Manual, 2009). For site-directed and multi-site mutagenesis using a single-stranded template, three unintended mutations were observed outside the region of the mutagenic oligonucleotides in 77 sequencing reactions of the 861 bp TEM-1 gene, which corresponds to an error rate of $4.5 \times 10^{-5}$. For the comprehensive codon mutagenesis, 6 mutations were observed outside the target region in CCM-1 and CCM-2, which corresponds to an error rate of $5.8 \times 10^{-5}$. These error rates are 35- and 45-fold higher than PfuTurbo Cx hotstart DNA polymerase's error rate. Without wishing to be bound to any one particular theory, it is thought that the elevated error rate results from deviations from the recommended PfuTurbo Cx reaction buffer and/or degradation of the ssDNA template at 95° C. All the observed unintended mutations can be explained by cytosine deamination (approximately $2 \times 10^{-7}$ events/sec at 95° C. in ssDNA (Lindahl and Nyberg, 1972) leading to G:C->A:T transitions or depurination (approximately $4 \times 10^{-7}$ events/sec at 95° C. in ssDNA (Lindahl and Nyberg, 1972; André et al., 1997) which can lead to various mutations.

Example 5

Figure 5:
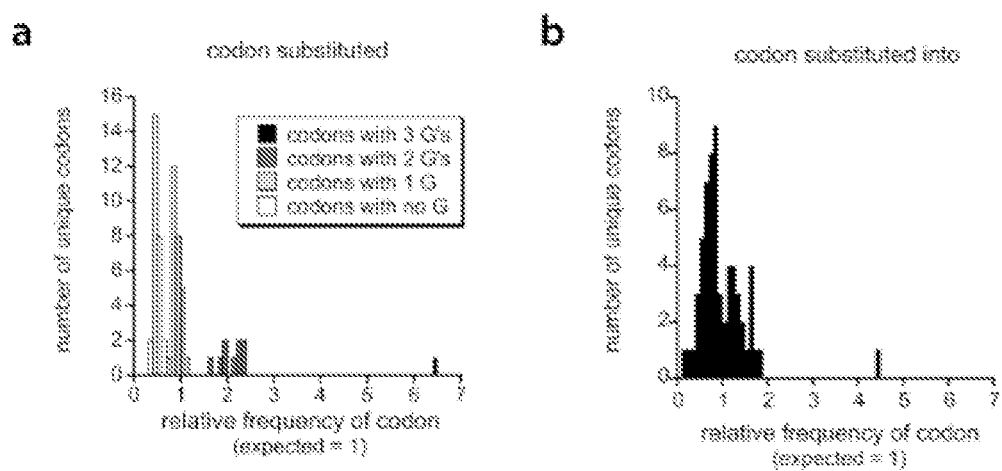

Identification of Adaptive Codon Substitutions in TEM-1 that Confer Increased Tazobactam Resistance with a Single Amino Acid Substitution An extensive knowledge of the possible molecular determinants of bacterial resistance to β-lactam antibiotics and β-lactamase inhibitors would inform the development and implementation of new antibiotics and inhibitors. Adaptive codon substitutions in TEM-1 were identified that conferred increased resistance to the (3-lactamase inhibitor tazobactam, which is used clinically in combination with the extended spectrum β-lactam antibiotic piperacillin in the drug Tazocin/Zosyn. These adaptive mutations were identified from library CCM-2—a second comprehensive codon mutagenesis library that was constructed which lacked the oligonucleotide-derived bias for G's in the substituted codon observed in CCM-1 (FIG. 5). CCM-2 was subjected to a selection for an increase in resistance to tazobactam. Under the selective conditions, wildtype survived at a frequency of about $10^{-3}$. Sequencing of 279 colonies revealed 120 unique non-wildtype sequences. Since any particular amino acid substitution is relatively rare in the library, the criteria that an amino acid substitution had to be observed twice was used to categorize it as potentially adaptive in nature. The set of these potentially adaptive substitutions (Table 6) overlapped one (M69L) but not other mutations previously found in alleles that increase tazobactam resistance, most notably R244S and N276D (Robin et al., 2011). In addition, 18 new, potentially adaptive amino acid substitutions, the most prevalent of which were 8 different amino acid substitutions at Y105 and the S235T mutation, were identified. The Y105 S/D/N and S235T mutations can occur with a single base change and are the most likely to appear naturally. These four mutations were introduced by single base substitution into TEM-1 and the ampicillin, piperacillin, and tazobactam resistance of these alleles were compared to previously known tazobactam resistance alleles (FIG. 6). Data for all replicates are shown in Tables 7 and 8. It was found that all four provide higher resistance to ampicillin in the presence of tazobactam than R244S and N276D, suggesting that the selection was too strong to identify R244S and N276D. The Y105N, Y105S, and S235T alleles showed significant inhibitor resistance for both ampicillin and piperacillin hydrolysis—at or above that of the M69L allele, which is the most resistant allele observed to date for the piperacillin/tazobactam combination (Robin et al., 2011). It is predicted that Y105N, Y105S, and S235T have the potential to emerge in the clinic. Without wishing to be bound to any one particular theory, it is believed that their nonemergence to date, and the fact that they were not identified in previous selections for tazobactam resistance performed on error prone PCR libraries (Vakulenko et al., 1998) may reflect the fact that the required base substitutions are not as common as the base substitutions for previously identified tazobactam resistance mutations. Again, without wishing to be bound to any one particular theory, it is thought that these mutations were readily identified by the presently disclosed methods because the PFunkel mutagenesis provides a less biased and much more comprehensive library of mutations than error prone PCR.

TABLE 6

Potential adaptive amino acid substitutions in TEM-1 identified from genetic selections for tazobactam resistance codon substitutions.

| Ambler position[a] | Amino acid substitutions | | | |
|---|---|---|---|---|
| | Clinically observed[b] | This Study[c] | Occurrences[d] | Codon coverage[e] |
| I13 | — | L | 2 | 2 of 6 |
| L21 | F,I | Q | 2 | 1 of 2 |
| M69 | L, I, V | L | 30 | 6 of 6 |
| Q90 | — | A | 2 | 1 of 4 |
| Y105 | — | G | 14 | 4 of 4 |
| | | S* | 10 | 3 of 6 |
| | | A | 7 | 2 of 4 |
| | | D | 5 | 2 of 2 |
| | | N | 5 | 2 of 2 |
| | | W | 4 | 1 of 1 |
| | | T | 2 | 2 of 4 |
| R120 | G | E | 3 | 1 of 2 |
| S124 | N | Q | 2 | 1 of 2 |
| T128 | — | E | 2 | 1 of 2 |
| T140 | — | G | 2 | 1 of 4 |
| E147 | — | G | 2 | 2 of 4 |
| W165 | R, C, G | Y | 4 | 2 of 2 |
| S235 | — | T | 8 | 3 of 4 |
| T265 | M | M | 4 | 1 of 1 |

[a]Numbering according to Ambler et al. (1998).

[b]Amino acid substitutions observed in natural alleles of TEM-1 with increased resistance to b-lactam antibiotics of β-lactamase inhibitors http://www.lahey.org/studies/temtable.asp). Amino acid substitutions underlined are found in alleles with increased inhibitor resistance (Drawz and Bonomo, 2010).

[c]Amino acid substitutions in bold were observed with a single based change in the codon.

*means that although the amino acid substitution can occur with a single base change, such a change was not observed here.

[d]Of the amino acid substitution in this study.

[e]For the amino acid substitutions found in this this study, the number of unique codons observed out of the possible number of unique codons is reported.

TABLE 7

Ampicillin MIC values for selected alleles.

| | MIC[a] ampicillin (µg/mL) | | | | | | | |
|---|---|---|---|---|---|---|---|---|
| | −tazobactam | | | | +tazobactam[b] | | | |
| Replicate | 1 | 2 | 3 | Median | 1 | 2 | 3 | Median |
| none | 8192 | 8192 | 8192 | 8192 | 16 | 22.6 | 22.6 | 22.6 |
| M69L | 5792 | 8192 | 8192 | 8192 | 512 | 724 | 724 | 724 |
| Y105D | 1448 | 1448 | 1448 | 1448 | 256 | 256 | 362 | 256 |
| Y105N | 4096 | 5792 | 5792 | 5792 | 148 | 1448 | 1448 | 1448 |
| Y105S | 2896 | 2896 | 2896 | 2896 | 724 | 1024 | 1024 | 1024 |
| S235T | 8192 | 8192 | 8192 | 8192 | 256 | 362 | 512 | 362 |
| R244S | 2896 | 4096 | 4096 | 4096 | 64 | 128 | 90.5 | 90.5 |
| N276D | 8192 | 8192 | 8192 | 8192 | 90.5 | 90.5 | 128 | 90.5 |

[a]Median value of three replicates. MIC assays performed in √2-fold increments (Mueller Hinton broth-agar, $10^4$ CFU/spot, 37° C. for 12 hours).

[b]tazobactam added to 6 µg/mL

TABLE 8

Piperacillin MIC values for selected alleles.

| | MIC[a] piperacillin (µg/mL) | | | | | | | |
|---|---|---|---|---|---|---|---|---|
| | −tazobactam | | | | +tazobactam[b] | | | |
| Replicate | 1 | 2 | 3 | Median | 1 | 2 | 3 | Median |
| none | 2896 | 2896 | 2896 | 2896 | 1 | 1.4 | 1.4 | 1.4 |
| M69L | 2048 | 2896 | 2896 | 2896 | 22.6 | 32 | 22.6 | 22.6 |
| Y105D | 1.4 | 1.4 | 1.4 | 1.4 | 1 | 1 | 1 | 1 |
| Y105N | 2048 | 2048 | 2048 | 2048 | 32 | 45 | 45 | 45 |
| Y105S | 1024 | 1448 | 1448 | 1448 | 16 | 16 | 16 | 16 |
| S235T | 2896 | 2896 | 2896 | 2896 | 32 | 16 | 22.6 | 22.6 |
| R244S | 1024 | 1448 | 1448 | 1448 | 2 | 2.83 | 2 | 2 |
| N276D | 2896 | 2896 | 2896 | 2896 | 1 | 1.4 | 2 | 1.4 |

[a]Median value of three replicates. MIC assays performed in √2-fold increments (Mueller Hinton broth-agar, $10^4$ CFU/spot, 37° C. for 12 hours).
[b]tazobactam added to 6 µg/mL

Example 6

PFunkel Mutagenesis Using a dsDNA Template

In some embodiments, the methods described above require that the gene targeted for mutation is in a phagemid (a plasmid containing the f1 phage origin) and require the production of phage particles from which the dU-ssDNA template is isolated. Although preparation of such a template is straightforward, the presently disclosed methods can be expanded to be applicable to any plasmid and to simplify the protocol by eliminating the need for phage entirely. The phageless PFunkel mutagenesis (FIG. 7, Table 9) achieves this by utilizing a dU-dsDNA plasmid template. After the mutation-containing second strand synthesis, UDG and ExoIII are added to degrade both strands of the dU-dsDNA template. The newly-synthesized, circular ssDNA is then converted to dsDNA using the reverse oligonucleotide. Like PFunkel mutagenesis using a ssDNA template, the reaction can be performed in a single tube using a thermocycler. Some of the major differences from the embodiment of the presently disclosed methods shown in FIG. 1 are the use of a dsDNA template instead of a ssDNA template and the degradation of the dU-containing template before the third strand synthesis.

PFunkel mutagenesis using a dsDNA template was tested for site-directed mutagenesis and multiple-site mutagenesis. For site-directed mutagenesis (using the c542a mutagenic primer), 708,000 transformants were obtained, and 10 of 10 randomly selected colonies had the desired mutation and no undesired mutations. For multiple-site mutagenesis, the creation of four specific mutations at distant sites in the gene was attempted. 445,000 transformants were obtained. Four of 10 colonies had all four mutations, the remainder either were wildtype (5 colonies) or had less than 4 mutations (1 colony). Without wishing to be bound to any one particular theory, it is believed that the apparent lower efficiency of multi-site mutagenesis using a dsDNA template may result from the difficulty in getting all four primers to simultaneously anneal to a dsDNA template (as opposed to a ssDNA template) or difficulty in degrading the dsDNA template.

TABLE 9

Reaction conditions for PFunkel mutagenesis using a dsDNA template.

| | Site-directed mutagenesis | Multiple-site mutagenesis |
|---|---|---|
| Start with | PfuTurbo Cx buffer<br>2.5 units PfuTurbo Cx polymerase<br>10 mM DTT<br>0.5 mM NAD+<br>0.2 mM dNTPs<br>1 µg (0.38 pmol) of dU-dsDNA<br>1 µL of 1.5 µM kinased mutagenic oligo<br>200 cohesive end units Taq ligase<br>100 µL total volume | PfuTurbo Cx buffer<br>1 µg (0.38 pmol) of dU- dsDNA<br>2 µL of 3 µM kinased mutagenic oligo mixture<br>77 µL total volume |
| Initial step | None | None |
| Cycling | 1 cycle of<br>95° C. for 3 min<br>55° C. for 90 sec<br>68° C. for 15 min | 95° C. for 3 min,<br>55° C. for 10 min<br>hold at 55° C.<br>add<br>10 mM DTT<br>0.5 mM NAD+,<br>0.2 mM dNTPs<br>2.5 units PfuTurbo Cx<br>(previously heat activated)<br>200 cohesive end units Taq ligase<br>bringing the total volume to<br>100 µL<br>65° C. for 15 min |

TABLE 9-continued

Reaction conditions for PFunkel mutagenesis using a dsDNA template.

| | Site-directed mutagenesis | Multiple-site mutagenesis |
|---|---|---|
| Ligation | 45° C. for 15 min | |
| Degradation of template and side-products | Shift to 37° C. Add 10 units of UDG + 30 units of ExoIII; incubate 1 hour at 37° C.; 70° C. for 20 min (heat inactivation) | Shift to 37° C. add 5 units of UDG + 2 units of ExoIII; incubate 1 hr at 37° C.; 70° C. for 20 min (heat inactivation) |
| add | Add 3.8 pmol of kinased oligo P320 (10:1 molar ratio oligo to template) | |
| Synthesis of second strand containing mutation | 1 cycle of 95° C. for 30 sec 55° C. for 45 sec 68° C. for 10 min 45° C. for 15 min (ligation) | |
| Final step | Purify DNA (optional step to increase number of transformants) and transform | |

Table 10 shows a comparison of PFunkel single-site mutagenesis with a single-stranded (PFunkel) and double-stranded (Phage-less PFunkel) template. The results show that using either the single-stranded or double-stranded template resulted in a 100% mutation rate. A comparison of multiple-site mutagenesis with a single-stranded (PFunkel) and double-stranded (Phage-less PFunkel) template also showed similar mutation rates (Table 11).

TABLE 10

PFunkel single mutagenesis with single-stranded (PFunkel) and double-stranded (Phage-less PFunkel) template
Single Mutation

| | PFunkel | Phage-less PFunkel |
|---|---|---|
| Template | ssDNA | dsDNA |
| Mutagenic Oligo | c542a | c542a |
| Colonies with mutation | 23 of 23 | 10 of 10 |
| Wild-type | 0 of 23 | 0 of 10 |
| Transformants | 533,000 | 708,000 |
| Template-degrading enzymes | 30 units exoIII | 30 units exoIII |

TABLE 11

PFunkel multiple site mutagenesis with single-stranded (PFunkel) and double-stranded (Phage-less PFunkel) template PFunkel Multi

| | | |
|---|---|---|
| Template | ssDNA | ssDNA |
| Mutagenic Oligos | A42G E104K M182T G238S | A42 (NNN) E104 (NNN) M182 (NNN) G238 (NNN) |
| Colonies with all positions mutated | 3 of 5 | 7 of 10 |
| Wild-type | 0 of 5 | 0 of 10 |
| Transformants | 1,440,000 | 5,840,000 |
| Template-degrading enzymes | 2 units exoIII | 2 units exoIII |

Phageless PFunkel Multi

| | | | |
|---|---|---|---|
| Template | dsDNA | dsDNA | dsDNA |
| Mutagenic Oligos | A42G E104K M182T G238S | A42 (NNN) E104 (NNN) M182 (NNN) G238 (NNN) | A42 (NNN) E104 (NNN) M182 (NNN) G238 (NNN) |
| Colonies with all positions mutated | 4 of 10 | 2 of 13 | 5 of 10 |
| Wild-type | 5 of 10 | 8 of 13 | 3 of 10 |
| Transformants | 445,000 | 140,000 | 160* |

TABLE 11-continued

PFunkel multiple site mutagenesis with single-stranded (PFunkel) and double-stranded (Phage-less PFunkel) template

| Template-degrading enzymes | 2 units exoIII | 2 units exoIII | 50 units ExoI 2 units ExoIII |
|---|---|---|---|

*5 µL of the unpurified reaction was transformed directly into chemically competent cells, therefore the number of transformants is lower.

Example 7

Discussion

The presently disclosed subject matter offers a very efficient method for site-directed mutagenesis at single or multiple-sites simultaneously. Once the template DNA is prepared, the method can be completed in a single day in a single tube, and requires no intermediate DNA purification or sub-cloning. PFunkel can be used for site-directed mutagenesis at an efficiency approaching 100%.

However, the real power of the PFunkel mutagenesis lies in the ability to make extensive, user defined libraries of single or multiple mutations. For example, there currently is no efficient method to make a library comprising all 5700 possible single amino acid mutations of a 300 amino acid long protein, nor is there a method to make a user-prescribed subset of 2000 of these 5700 mutations. The presently disclosed methods can be used for alanine scanning mutagenesis (Cunningham and Wells, 1989) to create all possible alanine substitutions, or a user-defined subset thereof in a single reaction. Expanding to scan all amino acids or all codons is equally simple. Mutating one or more specific sites simultaneously is also possible with ease. Comprehensive codon mutagenesis using PFunkel efficiently makes libraries for deep mutational scanning (Araya and Fowler, 2011) without the need for the costly and time-consuming construction of separate libraries for every codon analyzed. Compared to error prone PCR (Leung et al., 1989), which can practically access only approximately 30% of the possible amino acid substitutions in a gene, comprehensive codon mutagenesis allows effective access to all 100%.

The creation of a library with site-saturation at four distal sites simultaneously at 70% efficiency has been demonstrated herein. PFunkel mutagenesis has also been employed to create a comprehensive codon mutagenesis library of the TEM-1 β-lactamase gene. This library was designed to contain 18,081 members, one for each possible codon substitution in the gene (287 positions in TEM-1×63 possible codon substitutions). Deep sequencing revealed that approximately 97% of the designed single codon substitutions are present in the library. From such a library, 18 previously unreported adaptive mutations were identified, each of which confer resistance to the β-lactamase inhibitor tazobactam. Three of these mutations confer resistance equal to or higher than that of the most resistant reported TEM-1 allele and have the potential to emerge clinically.

For directed evolution studies, the generation of diversity by comprehensive codon mutagenesis allows access to unique mutational pathways not readily explored by current methods—enabling the identification of unique proteins with improved properties. PFunkel mutagenesis can efficiently create defined mutagenic diversity at multiple sites simultaneously and is thus tailor-made for the creation of computationally designed libraries for subsequent screening or selection strategies. All amino acids and codons can be accessed at any desired position.

PFunkel mutagenesis overcomes the limitations of currently available technology to offer a convenient, highly efficient and high-throughput approach for creating a user-defined library of gene mutants in which single or multiple mutations can be located anywhere in the gene.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Ambler R P, Coulson F W (1991) A Standard Numbering Scheme for the Class A Beta-Lactamases. Biochemical Journal Letters 276: 269-272;

André P, Kim A, Khrapko K, Thilly W G (1997) Fidelity and mutational spectrum of pfu DNA polymerase on a human mitochondrial DNA sequence. Genome Res 7: 843-852;

Araya C L, Fowler D M (2011) Deep mutational scanning assessing protein function on a massive scale. Trends Biotechnol 29: 435-442;

Baldwin, A. J., Busse, K., Simm, A. M., & Jones, D. D. (2008). Expanded molecular diversity generation during directed evolution by trinucleotide exchange (trinex). Nucleic Acids Res, 36(13), e77;

Bi, W., & Stambrook, P. J. (1998). Site-Directed mutagenesis by combined chain reaction. Anal Biochem, 256(1), 137-40;

Blankenberg D, Von Kuster G, Coraor N, Ananda G, Lazarus R, Mangan M, Nekrutenko A, Taylor J. "Galaxy: a web-based genome analysis tool for experimentalists". Current Protocols in Molecular Biology. 2010 January; Chapter 19:Unit 19.10.1-21;

Chung, C. T., Niemela, S. L., & Miller, R. H. (1989). One-Step preparation of competent *Escherichia coli*: Transformation and storage of bacterial cells in the same solution. Proc Natl Acad Sci USA, 86(7), 2172-5;

Cunningham B C, Wells J A (1989) High-resolution epitope mapping of hGHreceptor interactions by alanine-scanning mutagenesis. Science 244: 1081-1085;

Denbigh K G (1944) Velocity and yield in continuous reaction systems. Trans. Faraday Soc 40: 352-373;

Dominy C N, Andrews D W (2003) Site-Directed mutagenesis by inverse PCR. Methods Mol Biol 235:209-23;

Drawz S M, Bonomo R A (2010) Three decades of β-lactamase inhibitors. Clin Microbiol Rev 23: 160;

Giardine B, Riemer C, Hardison R C, Burhans R, Elnitski L, Shah P, Zhang Y, Blankenberg D, Albert I, Taylor J, Miller W, Kent W J, Nekrutenko A. "Galaxy: a platform for interactive large-scale genome analysis." Genome Research. 2005 October; 15(10):1451-5;

Goecks, J, Nekrutenko, A, Taylor, J and The Galaxy Team. Galaxy: a comprehensive approach for supporting accessible, reproducible, and transparent computational research in the life sciences. Genome Biol. 2010 Aug. 25; 11(8):R86;

Hames, C., Halbedel, S., Schilling, O., & Stülke, J. (2005). Multiple-Mutation reaction: A method for simultaneous introduction of multiple mutations into the glpk gene of *Mycoplasma pneumoniae*. Appl Environ Microbiol, 71(7), 4097-100;

Hogrefe, H. H., Cline, J., Lovejoy, A. E., & Nielson, K. B. (2001). DNA polymerases from hyperthermophiles. Methods Enzymol, 334, 91-116;

Holland, M. M., McQuillan, M. R., & O'Hanlon, K. A. (2011). Second generation sequencing allows for mtdna mixture deconvolution and high resolution detection of heteroplasmy. Croat Med J, 52(3), 299-313;

Holland M M, McQuillan M R, O'Hanlon K A (2011) Second generation sequencing allows for mtdna mixture deconvolution and high resolution detection of heteroplasmy. Croat Med J 52: 299-313;

Kunkel, T. A. (1985). Rapid and efficient site-specific mutagenesis without phenotypic selection. Proc Natl Acad Sci USA, 82(2), 488-92;

Kunkel, T. A., Bebenek, K., & McClary, J. (1991). Efficient site-directed mutagenesis using uracil-containing DNA. Methods Enzymol, 204, 125-39;

Kunkel, T. A., Roberts, J. D., & Zakour, R. A. (1987). Rapid and efficient site-specific mutagenesis without phenotypic selection. Methods Enzymol, 154, 367-82.;

Leung D W, Chen E, Goeddel D V (1989) A method for random mutagenesis of a defined DNA segment using a modified polymerase chain reaction. Technique 1: 11-15;

Lindahl T, Nyberg B (1972) Rate of depurination of native deoxyribonucleic acid. Biochemistry 11: 3610-3618;

Lindahl T, Nyberg B (1974) Heat-Induced deamination of cytosine residues in deoxyribonucleic acid. Biochemistry 13: 3405-3410;

Liu, J., & Cropp, T. A. (2012). A method for multi-codon scanning mutagenesis of proteins based on asymmetric transposons. Protein Eng Des Sel, 25(2), 67-72;

Meyerhans, A., Vartanian, J. P., & Wain-Hobson, S. (1990). DNA recombination during PCR. Nucleic Acids Res, 18(7), 1687-91;

Murakami, H., Hohsaka, T., & Sisido, M. (2002). Random insertion and deletion of arbitrary number of bases for codon-based random mutation of dnas. Nat Biotechnol, 20(1), 76-81;

Nørholm, M. H. (2010). A mutant pfu DNA polymerase designed for advanced uracil-excision DNA engineering. BMC Biotechnol, 10, 21;

PfuTurbo Cx hotstart DNA polymerase Instruction Manual, (2009) Catalog #600410, Revision A.01. Agilent Technologies;

QuikChange Multi Site-Directed Mutagenesis Kit, Instruction Manual, Catalog #200514, Revision #124003a, Stratagene;

QuikChange Site-Directed Mutagenesis Kit, Instruction Manual, Catalog #200518, Revision #B.01, Stratagene;

Robin F, Krebs M, Delmas J, Mirande C, Bonnet R (2011) In vitro efficiency of the piperacillin/tazobactam combination against inhibitor-resistant TEM and complex mutant TEM-producing clinical strains of Escherichia coli. J Antimicrob Chemother 66: 1052-1056.

Rogers, S. G., & Weiss, B. (1980). Exonuclease III of Escherichia coli K-12, an AP endonuclease. Methods Enzymol, 65(1), 201-11.

Sambrook, MacCallum, & Russell (2001). Molecular cloning: A laboratory manual (3 ed.). Cold Spring Harbor Laboratory Press.

Scholle, M. D., Kehoe, J. W., & Kay, B. K. (2005). Efficient construction of a large collection of phage-displayed combinatorial peptide libraries. Comb Chem High Throughput Screen, 8(6), 545-51.

Sohka, T., Heins, R. A., Phelan, R. M., Greisler, J. M., Townsend, C. A., & Ostermeier, M. (2009). An externally tunable bacterial band-pass filter. Proc Natl Acad Sci USA, 106(25), 10135-40.

Taylor, A. F., & Weiss, B. (1982). Role of exonuclease III in the base excision repair of uracil-containing DNA. J Bacteriol, 151(1), 351-7.

Trower, M. K. (1994). Site-directed mutagenesis using a uracil-containing phagemid template. Methods Mol Biol, 31, 67-77.

Vakulenko S B, Geryk B, Kotra L P, Mobashery S, Lerner S A (1998) Selection and characterization of beta-lactam-beta-lactamase inactivator-resistant mutants following PCR mutagenesis of the TEM-1 beta-lactamase gene. Antimicrob Agents Chemother 42: 1542-1548.

Wassman, C. D., Tam, P. Y., Lathrop, R. H., & Weiss, G. A. (2004). Predicting oligonucleotide-directed mutagenesis failures in protein engineering. Nucleic Acids Res, 32(21), 6407-13.

Weiss, G. A., Watanabe, C. K., Zhong, A., Goddard, A., & Sidhu, S. S. (2000). Rapid mapping of protein functional epitopes by combinatorial alanine scanning. Proc Natl Acad Sci USA, 97(16), 8950-4.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A method for introducing one or more mutations to a single-stranded target nucleic acid molecule, said method comprising:
    a) conducting a first amplification reaction in the presence of a thermostable DNA polymerase and a thermostable DNA ligase at an elevated temperature to synthesize a mutagenized strand of DNA comprising at least one mutagenic oligonucleotide relative to a complementary single-stranded uracil-containing template comprising a target nucleic acid molecule in a circular DNA vector;
    b) conducting a second amplification reaction in the presence of a thermostable DNA polymerase and a thermostable DNA ligase at an elevated temperature to synthesize a complementary mutant strand of DNA; and
    c) degrading the uracil-containing DNA and non-covalently closed circular nucleic acid molecules at an elevated temperature to obtain a mutation-containing double-stranded DNA product.

2. The method of claim 1, further comprising annealing at least one mutagenic oligonucleotide comprising at least one mutation to the target nucleic acid molecule at a first elevated temperature before conducting the first amplification reaction.

3. The method of claim 2, wherein the first amplification reaction is conducted in the presence of the thermostable DNA polymerase and the thermostable DNA ligase at a second elevated temperature to synthesize the mutagenized strand of DNA comprising the at least one mutagenic oligonucleotide.

4. The method of claim 3, further comprising denaturing the mutagenized strand of DNA at a third elevated temperature before conducting the second amplification reaction.

5. The method of claim 4, further comprising annealing a reverse primer to the mutagenized strand of DNA at a fourth elevated temperature after denaturing the mutagenized strand of DNA and before conducting the second amplification reaction.

6. The method of claim 5, wherein the second amplification reaction is conducted in the presence of the thermostable DNA polymerase and the thermostable DNA ligase at a fifth elevated temperature to synthesize the complementary mutant strand of DNA.

7. The method of claim 6, wherein degrading the uracil-containing DNA and non-covalently closed circular nucleic acid molecules is conducted at a sixth elevated temperature to obtain the mutation-containing double-stranded DNA product.

8. The method of claim 7, wherein at least one or more of:
    the first elevated temperature is from about 50° C. to about 60° C.;
    the second elevated temperature is from about 60° C. to about 73° C.;
    the third elevated temperature is from about 90° C. to about 98° C.;
    the fourth elevated temperature is from about 50° C. to about 60° C.;
    the fifth elevated temperature is about 60° C. to about 73° C.; and
    the sixth elevated temperature is from about 32° C. to about 42° C.

9. The method of claim 1, wherein the target nucleic acid molecule is denatured at a temperature from about 90° C. to about 98° C. before annealing the at least one mutagenic oligonucleotide to the target nucleic acid molecule.

10. The method of claim 1, wherein the thermostable DNA polymerase is PfuTurbo Cx.

11. The method of claim 1, wherein the thermostable DNA ligase is selected from the group consisting of Pfu DNA ligase, Tth DNA ligase, Taq DNA ligase, *Thermus filiformis* ligase, *Rhodothermus marinus* DNA ligase, *Thermus scotoductus* DNA ligase and *Bacillus stearothermophilus* DNA ligase.

12. The method of claim 1, wherein at least one or more of the annealing the at least one mutagenic oligonucleotide step, the first amplification reaction step, the annealing the reverse primer step, and the second amplification reaction step, are performed at the same time by thermal cycling.

13. The method of claim 1, wherein the annealing the at least one mutagenic oligonucleotide step and the first amplification reaction step are performed more than once before the step of denaturing the mutagenized strand of DNA occurs, and wherein at least one additional mutagenic oligonucleotide is added to the reaction in a stepwise manner.

14. The method of claim 1, wherein at least one or more of a further step after the first amplification reaction step and before the denaturing step comprises completing the ligation at a temperature from about 40° C. to about 50° C. and a further step after the second amplification reaction step and before the degrading step comprises completing the ligation at a temperature from about 40° C. to about 50° C.

15. The method of claim 1, wherein the mutation-containing double-stranded DNA product comprises one mutation.

16. The method of claim 15, wherein the efficiency of mutagenesis is about 98% or greater and the molar ratio of mutagenic oligonucleotide to single-stranded uracil-containing template is from about 1:1 to about 100:1.

17. The method of claim 1, wherein the mutation-containing double-stranded DNA product comprises more than one mutation.

18. The method of claim 1, wherein the mutation-containing double-stranded DNA product comprises a gene.

19. The method of claim 18, wherein a non-comprehensive or comprehensive codon mutagenesis library is created.

20. The method of claim 1, wherein the at least one mutation is a substitution mutation, a deletion, or an addition of a DNA base.

21. The method of claim 1, further comprising transforming a host cell with the DNA product from the degrading step.

22. The method of claim 21, wherein the DNA product is purified before being transformed into the host cell.

23. The method of claim 1, wherein uracil DNA glycosylase and exonuclease III are used to degrade the uracil-containing DNA and non-covalently closed circular nucleic acid molecules.

24. A method for introducing one or more mutations to a double-stranded target nucleic acid molecule, the method comprising:
  (a) conducting a first amplification reaction in the presence of a thermostable DNA polymerase and a thermostable DNA ligase at an elevated temperature to synthesize a mutagenized strand of DNA comprising at least one mutagenic oligonucleotide relative to at least one complementary strand of a double-stranded uracil-containing template comprising a target nucleic acid molecule in a circular DNA vector;
  (b) degrading the uracil-containing DNA and non-covalently closed circular nucleic acid molecules at an elevated temperature; and
  (c) conducting a second amplification reaction in the presence of a thermostable DNA polymerase and a thermostable DNA ligase at an elevated temperature to synthesize a complementary mutant strand of DNA and obtain a mutation-containing double-stranded DNA product.

25. The method of claim 24, further comprising denaturing the target nucleic acid molecule at a first elevated temperature before conducting the first amplification reaction.

26. The method of claim 25, further comprising annealing the at least one mutagenic oligonucleotide comprising the at least one mutation to the target nucleic acid molecule at a second elevated temperature after denaturing the target nucleic acid molecule and before conducting the first amplification reaction.

27. The method of claim 26, wherein the first amplification reaction is conducted in the presence of the thermostable DNA polymerase and the thermostable DNA ligase at a third elevated temperature to synthesize the mutagenized strand of DNA comprising the at least one mutagenic oligonucleotide.

28. The method of claim 27, further comprising denaturing the mutagenized strand of DNA at a fifth elevated temperature after degrading the uracil-containing DNA and non-covalently closed circular nucleic acid molecules.

29. The method of claim 28, further comprising annealing a reverse primer to the denatured mutagenized strand of DNA at a sixth elevated temperature before conducting the second amplification reaction.

30. The method of claim 29, wherein the second amplification reaction is conducted in the presence of the thermostable DNA polymerase and the thermostable DNA ligase at a seventh elevated temperature to synthesize the complementary mutant strand of DNA and obtain the mutation-containing double-stranded DNA product.

31. The method of claim 30, wherein at least one or more of:
  the first elevated temperature is from about 90° C. to about 98° C.;
  the second elevated temperature is from about 50° C. to about 60° C.;
  the third elevated temperature is from about 60° C. to about 73° C.;
  the fourth elevated temperature is from about 32° C. to about 42° C.;
  the fifth elevated temperature is from about 90° C. to about 98° C.;
  the sixth elevated temperature is from about 50° C. to about 60° C.; and
  the seventh elevated temperature is from about 60° C. to about 73° C.

32. The method of claim 24, wherein the thermostable DNA polymerase is PfuTurbo Cx.

33. The method of claim 24, wherein the thermostable DNA ligase is selected from the group consisting of: Pfu DNA ligase, Tth DNA ligase, Taq DNA ligase, *Thermus filiformis* ligase, *Rhodothermus marinus* DNA ligase, *Thermus scotoductus* DNA ligase and *Bacillus stearothermophilus* DNA ligase.

34. The method of claim 24, wherein at least one or more of the annealing the at least one mutagenic oligonucleotide step, the first amplification reaction step, the annealing the reverse primer step, and the second amplification reaction step are performed at the same time.

35. The method of claim 24, wherein the annealing the at least one mutagenic oligonucleotide step and the first amplification reaction step are performed more than once before the degrading step occurs, and wherein at least one additional mutagenic oligonucleotide is added to the reaction in a stepwise manner.

36. The method of claim 24, wherein at least one or more of a further step after the first amplification reaction step and before the degrading step and a further step after the second amplification reaction step comprises completing the ligation at a temperature from about 40° C. to about 50° C.

37. The method of claim 24, wherein the mutation-containing double-stranded DNA product comprises one mutation and the efficiency of mutagenesis is about 98% or greater.

38. The method of claim 37, wherein the molar ratio of mutagenic oligonucleotide to double-stranded uracil-containing template is from about 1:1 to about 100:1.

39. The method of claim 24, wherein the mutation-containing double-stranded DNA product comprises more than one mutation.

40. The method of claim 24, wherein the mutation-containing double-stranded DNA product comprises a gene.

41. The method of claim 40, wherein a non-comprehensive or comprehensive codon mutagenesis library is created.

42. The method of claim 41, wherein the non-comprehensive or comprehensive codon mutagenesis library is used to obtain an improved protein, gene or gene promoter.

43. The method of claim 24, wherein the at least one mutation is a substitution mutation, a deletion, or an addition of a DNA base.

44. The method of claim 24, further comprising transforming a host cell with the DNA product from step (c).

45. The method of claim 44, wherein the DNA product is purified before being transformed into the host cell.

46. The method of claim 24, wherein uracil DNA glycosylase and exonuclease III are used to degrade the uracil-containing DNA and non-covalently closed circular nucleic acid molecules.

47. The method of claim 19, wherein the non-comprehensive or comprehensive codon mutagenesis library is used to obtain an improved protein, gene or gene promoter.

* * * * *